(12) United States Patent
Sobel et al.

(10) Patent No.: US 12,138,067 B2
(45) Date of Patent: Nov. 12, 2024

(54) CHARACTERIZATION OF THE NASAL CYCLE

(71) Applicant: Noam Sobel, Tel Aviv (IL)

(72) Inventors: Noam Sobel, Tel Aviv (IL); Kobi Snitz, Tel Aviv (IL); Danielle Honigstein, Jerusalem (IL); Aharon Weissbrod, Rehovot (IL)

(73) Assignee: Noam Sobel, Tel Aviv (IL)

( * ) Notice: Subject to any disclaimer, the term of this patent is extended or adjusted under 35 U.S.C. 154(b) by 774 days.

(21) Appl. No.: 17/380,348

(22) Filed: Jul. 20, 2021

(65) Prior Publication Data

US 2023/0028914 A1    Jan. 26, 2023

(51) Int. Cl.
A61B 5/00        (2006.01)
A61B 5/087       (2006.01)

(52) U.S. Cl.
CPC .......... *A61B 5/4035* (2013.01); *A61B 5/0002* (2013.01); *A61B 5/087* (2013.01); *A61B 5/4561* (2013.01); *A61B 5/6819* (2013.01); *A61B 5/6822* (2013.01); *A61B 2562/0247* (2013.01)

(58) Field of Classification Search
CPC ..... A61B 5/4035; A61B 5/0002; A61B 5/087; A61B 5/4561; A61B 5/6819; A61B 5/6822; A61B 2562/0247; A61B 5/097; A61B 5/6814
See application file for complete search history.

(56) References Cited

U.S. PATENT DOCUMENTS

2007/0186929 A1    8/2007  Aylsworth

FOREIGN PATENT DOCUMENTS

| CN | 105997090 A | 10/2016 |
|----|-------------|---------|
| CN | 209018736 U | 6/2019 |
| CN | 209474618 U | 11/2019 |
| CN | 211483071 U | 9/2020 |
| CN | 211610290 U | 10/2020 |

(Continued)

OTHER PUBLICATIONS

Roni Kahana-Zweig, "Measuring and Characterizing the Human Nasal Cycle", PLOS One/journal.pone.0162918 Oct. 6, 2016.

(Continued)

*Primary Examiner* — Jonathan T Kuo
(74) *Attorney, Agent, or Firm* — CANTOR COLBURN LLP

(57) ABSTRACT

Apparatus is provided that includes left-nostril, right-nostril, and oral pressure sensors and oral pressure probes. A memory is configured to store left-nostril, right-nostril, and oral pressures sensed by the respective sensors, over a total period of at least 12 hours. A processor is configured to convert the left-nostril, right-nostril, and oral pressures stored in the memory to left-nostril, right-nostril, and oral pressure airflows, respectively, and calculate a series of orally-weighted laterality-indices over a respective series of sub-periods of the total period. Each of the orally-weighted laterality-indices of each of the sub-periods is indicative of a laterality index over the sub-period weighted by a normalized oral airflow over the sub-period, such that the greater the normalized oral airflow, the smaller the orally-weighted laterality-index. Each of the orally-weighted laterality-indices of each of the sub-periods reflects relative airflow through the left and the right nostrils over the sub-period. Other embodiments are also described.

22 Claims, 13 Drawing Sheets

(56) References Cited

FOREIGN PATENT DOCUMENTS

| GB | 2540727 A | 2/2017 |
|---|---|---|
| KR | 1020140132541 A | 11/2014 |
| KR | 1020170100700 A | 9/2017 |
| KR | 1020190093847 A | 8/2019 |
| KR | 102074486 B1 | 2/2020 |
| WO | 9705824 A1 | 2/1997 |
| WO | 2019193382 A1 | 10/2019 |

OTHER PUBLICATIONS

An Invitation to pay additional fees dated Oct. 6, 2022, which issued during the prosecution of Applicant's PCT/IL2022/050773.
International Search Report for corresponding application PCT/IL2022/050773 filed Jul. 19, 2022; Mail date Nov. 28, 2022.
Written Opinion for corresponding application PCT/IL2022/050773 filed Jul. 19, 2022; Mail date Nov. 28, 2022.

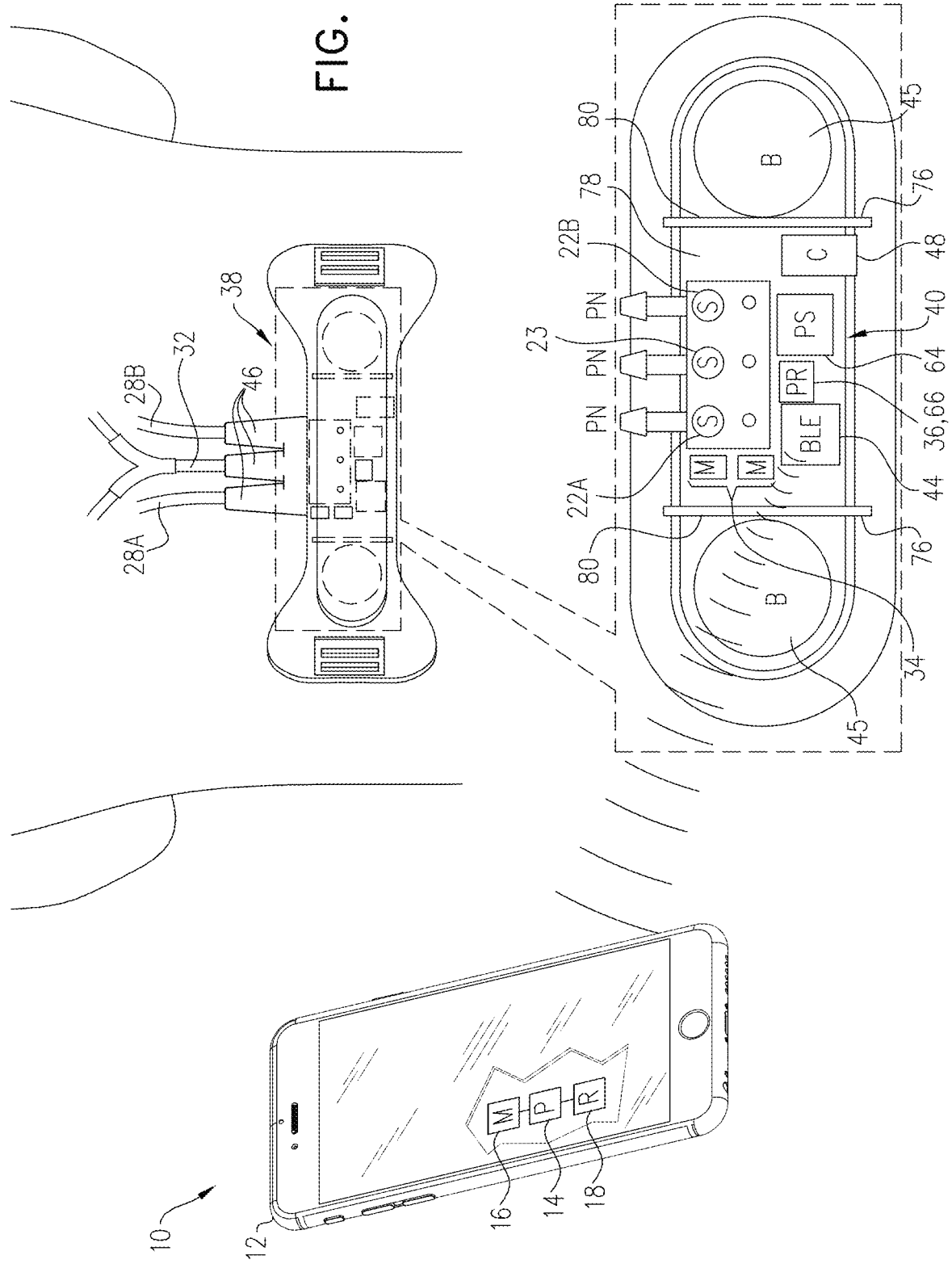

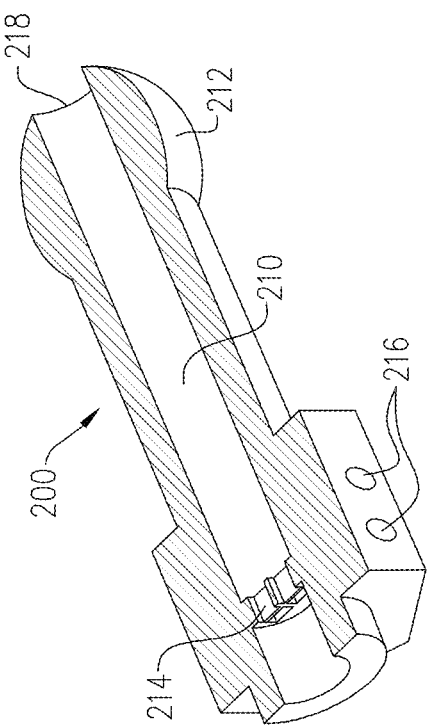
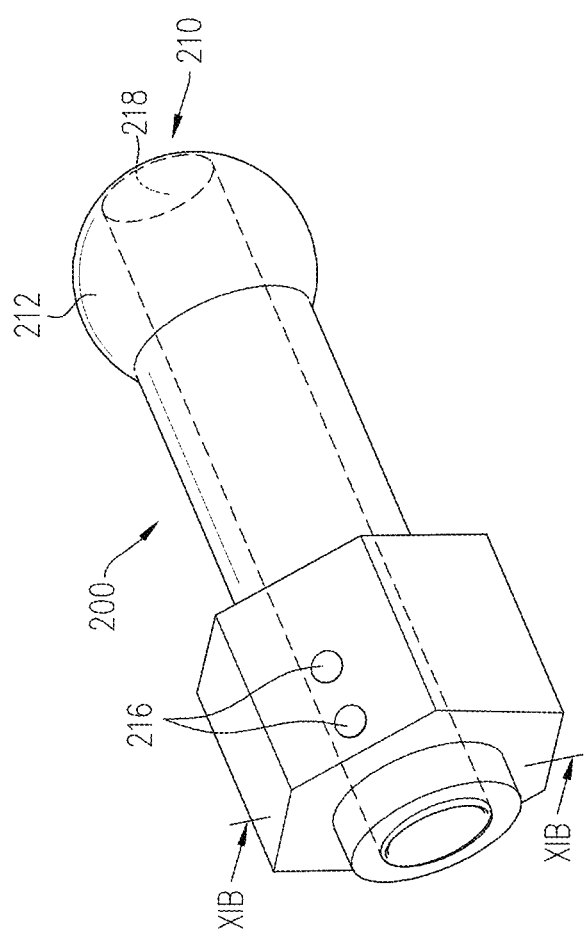
FIG. 11B
FIG. 11A

CHARACTERIZATION OF THE NASAL CYCLE

FIELD OF THE APPLICATION

The present invention relates generally to devices and techniques for measuring and characterizing the nasal cycle.

BACKGROUND OF THE APPLICATION

Cyclic events constitute a fundamental aspect of biological function at levels ranging from subcellular components to the entire organism. One such large-scale cycle evident in mammals is known as the nasal cycle, in which nasal airflow is greater in one nostril than in the other, and the greater-airflow nostril shifts between left and right over time.

The physical mechanism underlying the nasal cycle is an asymmetry in blood flow leading to engorgement of erectile tissue in the anterior part of the nasal septum and inferior turbinate of one nostril over the other. This asymmetrically enlarged tissue physically blocks the passage of air in one nostril more than in the other. Although this physical mechanism has been identified, the physiological mechanisms that drive it are not well understood.

These mechanisms are clearly related to the autonomic nervous system in that unilateral sympathetic dominance is associated with vasoconstriction and decongestion in one nostril, while simultaneous parasympathetic dominance is associated with vasodilatation and congestion in the other. In other words, measurement of asymmetry of airflow in the nose can provide an indication regarding balance/imbalance in the autonomic nervous system. The nasal cycle can change with body posture, changes with age, is related to handedness, and is also reflected in a host of brain activity measures such as electroencephalography (EEG) and cognitive-task performance. The nasal cycle is altered in a host of neurological and non-neurological conditions including high spinal cord injuries, autism, Parkinson's disease, schizophrenia, Kallmann's syndrome, cardiac symptoms, fever, and electrolyte imbalance. Finally, the nasal cycle is also related to various physiological measures beyond alterations in disease alone, such as heart rate and blood pressure, blood glucose levels, intraocular pressure, blink rate, and alternating lateralization of plasma catecholamines. Thus, characterization of the nasal cycle may have significant diagnostic value for neurological conditions and other purposes.

Kahana-Zweig R et al., in "Measuring and Characterizing the Human Nasal Cycle," PLoS One 2016 Oct. 6; 11(10): e0162918, which is incorporated herein by reference, provide detailed instructions for constructing a tool allowing continuous accurate measurement and recording of airflow in each nostril separately at minimal cost and effort. They demonstrate application of the tool in 33 right-handed healthy subjects, and derive several statistical measures for nasal cycle characterization. Using these measures applied to 24-hour recordings they observed that: 1: subjects spent slightly longer in left over right nostril dominance (left=2.63±0.89 hours, right=2.17±0.89 hours, t(32)=2.07, p<0.05), 2: cycle duration was shorter in wake than in sleep (wake=2.02±1.7 hours, sleep=4.5±1.7 hours, (t(30)=5.73, p<0.0001). 3: slower breathing was associated with a more powerful cycle (the extent of difference across nostrils) (r=0.4, p<0.0001), and 4: the cycle was influenced by body posture such that lying on one side was associated with greater flow in the contralateral nostril (p<0.002). Finally, they provide evidence for an airflow cycle in each nostril alone. These results are described as providing characterization of an easily obtained measure that may have diagnostic implications for neurological disease and cognitive state.

SUMMARY OF THE APPLICATION

Some embodiments of the present invention provide a nasal-cycle characterization device that is configured to ascertain the nasal cycle of subject. The nasal cycle is a measure of airflow asymmetry that may be indicative of balance in the autonomic nervous system. The device separately and continuously records airflow from three sources: the left nostril, the right nostril, and the mouth. The device comprises three independent sensors independently coupled to a nasal/oral probe. The device is configured to calculate an orally-weighted laterality-index (OWLI) that weights the laterality of airflow between the left and right nostrils by normalized oral airflow, such that the greater the normalized oral airflow, the smaller the orally-weighted laterality-index.

Although typically reciprocal, each nostril can also cycle independently, and both nostrils can shift to the closed state, thus forcing mouth-breathing. This can happen mostly at night. Without the oral-weighting techniques described herein, a "zero signal" measured in both nostrils can indicate either that both nostrils have closed and the person is mouth-breathing, or that the person is in a state of apnea, not breathing at all. The oral-weighting techniques described herein allow discrimination between these two states. This allows for faithful nasal cycle characterization.

For some applications, the nasal-cycle characterization device is configured to also continuously sense and log both body and head posture. To this end, the device comprises a posture-sensing unit that is configured to separately sense body posture and head posture. It has been demonstrated that the nasal cycle shifts with body and/or head posture. Thus, simultaneously recording posture of both the body and the head provides useful information in combination with the techniques described herein for nasal-cycle characterization. Body and head posture are mostly the same, accept in one yet critical phase: while sleeping, and primarily on the stomach, the head can turn either left, hence left nostril up, or right, hence right nostril up. This may represent important information for understanding shifts in the nasal cycle, so it may be useful to obtain and log this information.

There is therefore provided, in accordance with an application of the present invention, apparatus including:
 a left-nostril pressure sensor, a right-nostril pressure sensor, and an oral pressure sensor;
 a nostril-oral probe, which includes:
  a left-nostril pressure probe, which is configured to be inserted into a left nostril of a subject, and includes a left-nostril-pressure tube that is configured to transmit a left-nostril pressure wave from the left nostril to the left-nostril pressure sensor;
  a right-nostril pressure probe, which is configured to be inserted into a right nostril of the subject, and includes a right-nostril-pressure tube that is configured to transmit a right-nostril pressure wave from the right nostril to the right-nostril pressure sensor; and
  an oral pressure probe, which is configured to be positioned in air communication with a mouth of the subject, and includes an oral-pressure tube that is configured to transmit an oral pressure wave from the mouth to the oral pressure sensor;

a memory, which is configured to store left-nostril, right-nostril, and oral pressures sensed by the left-nostril pressure sensor, the right-nostril pressure sensor, and the oral pressure sensor, respectively, over a total period having a duration of at least 12 hours; and one or more processors, which are configured:
  to convert the left-nostril, the right-nostril, and the oral pressures stored in the memory to left-nostril, right-nostril, and oral pressure airflows, respectively, and
  to calculate, based on the left-nostril, the right-nostril, and the oral airflows, a series of orally-weighted laterality-indices over a respective series of sub-periods of the total period,
    wherein each of the orally-weighted laterality-indices of each of the sub-periods is indicative of a laterality index over the sub-period weighted by a normalized oral airflow over the sub-period, such that the greater the normalized oral airflow, the smaller the orally-weighted laterality-index, and
    wherein each of the orally-weighted laterality-indices of each of the sub-periods reflects relative airflow through the left and the right nostrils over the sub-period.

For some applications, the one or more processors are configured to calculate an overall orally-weighted laterality index equal to an average of the orally-weighted laterality-indices during the total period.

For some applications, the apparatus further includes a wireless transmitter, which is configured to transmit a wireless signal indicative of the overall orally-weighted laterality index.

For some applications, the one or more processors are configured to calculate an overall orally-weighted laterality index equal to an average of respective absolute values of the orally-weighted laterality-indices during the total period.

For some applications, each of the sub-periods has a duration of between 30 and 180 seconds.

For some applications, the duration of the total period is at least 24 hours.

For some applications, the oral pressure probe is configured to be positioned outside the mouth in the air communication with the mouth.

For some applications:
  the apparatus further includes a posture sensor that is configured to separately sense body posture and head posture, and
  the one or more processors are configured to calculate each of the orally-weighted laterality-indices of each of the sub-periods partially in response to the sensed body posture and the sensed head posture such that each of the sub-periods is associated with a given combination of the sensed body posture and head posture.

For some applications, the apparatus further includes a wireless transmitter, which is configured to transmit wireless signals indicative of the left-nostril, the right-nostril, and the oral pressures.

For some applications, the apparatus further includes a wireless transmitter, which is configured to transmit wireless signals indicative of the series of orally-weighted laterality-indices.

For some applications, the apparatus further includes one or more batteries.

For some applications, the one or more processors are configured to calculate each of the laterality indices of each of the sub-periods by dividing (a) a difference between the left-nostril airflow and the right-nostril airflow over the sub-period by (b) a sum of the left-nostril airflow and the right-nostril airflow over the sub-period.

For some applications, the one or more processors are configured to weight each of the orally-weighted laterality-indices of each of the sub-periods by multiplying (a) the laterality index by (b) (i) a difference between 1 and an absolute value of the normalized oral airflow, over the sub-period (ii) raised to a power less than 1. For some applications, the power is no more than 0.5. For some applications, the power equals 0.25.

For some applications, the apparatus further includes:
  a housing, configured to be coupled to skin of a nape of a subject; and
  exactly one position sensor, which is configured to sense a position of the position sensor with at least three degrees of freedom and provide at least three position-sensor outputs, and which is disposed within the housing,
  wherein the one or more processors are configured to:
    ascertain, using the position-sensor outputs when the housing is coupled to the skin of the nape, body posture of the subject and, separately, head posture of the subject, and
    generate one or more posture outputs indicative of the body posture and the head posture.

For some applications, the apparatus further includes:
  a housing, configured to be coupled to skin of a nape of a subject; and
  at least one position sensor, which is configured to sense a position of the position sensor and provide position-sensor outputs, and is disposed within the housing,
  wherein the one or more processors are configured to:
    ascertain, using the position-sensor outputs when the housing is coupled to the skin of the nape, body posture of the subject and, separately, head posture of the subject,
    based on the body posture and the head posture, select a combined posture of the subject from a plurality of predetermined possible combined postures that reflect both the body posture and the head posture, wherein the one or more processors are configured such that the plurality of predetermined possible combined postures includes: upright, lying with a face facing left, and lying with the face facing right, and
    generate a posture output indicative of the combined posture of the subject.

There is further provided, in accordance with an application of the present invention, a method including:
  inserting a left-nostril pressure probe of a nostril-oral probe into a left nostril of a subject, such that a left-nostril-pressure tube transmits a left-nostril pressure wave from the left nostril to a left-nostril pressure sensor;
  inserting a right-nostril pressure probe of the nostril-oral probe into a right nostril of the subject, such that a right-nostril-pressure tube transmits a right-nostril pressure wave from the right nostril to a right-nostril pressure sensor;
  positioning an oral pressure probe of the nostril-oral probe in air communication with a mouth of the subject, such that an oral-pressure tube transmits an oral pressure wave from the mouth to an oral pressure sensor; and
  activating one or more processors:
    to store, in a memory, left-nostril, right-nostril, and oral pressures sensed by the left-nostril pressure sensor, the right-nostril pressure sensor, and the oral pressure sensor, respectively, over a total period having a duration of at least 12 hours,
to convert the left-nostril, the right-nostril, and the oral pressures stored in the memory to left-nostril, right-nostril, and oral pressure airflows, respectively, and
to calculate, based on the left-nostril, the right-nostril, and the oral airflows, a series of orally-weighted laterality-indices over a respective series of sub-periods of the total period,
wherein each of the orally-weighted laterality-indices of each of the sub-periods is indicative of a laterality index over the sub-period weighted by a normalized oral airflow over the sub-period, such that the greater the normalized oral airflow, the smaller the orally-weighted laterality-index, and
wherein each of the orally-weighted laterality-indices of each of the sub-periods reflects relative airflow through the left and the right nostrils over the sub-period.

For some applications, activating the one or more processors includes activating the one or more processors to calculate an overall orally-weighted laterality index equal to an average of the orally-weighted laterality-indices during the total period.

For some applications, activating the one or more processors includes activating the one or more processors to transmit a wireless signal indicative of the overall orally-weighted laterality index.

For some applications, activating the one or more processors includes activating the one or more processors to calculate an overall orally-weighted laterality index equal to an average of respective absolute values of the orally-weighted laterality-indices during the total period.

For some applications, each of the sub-periods has a duration of between 30 and 180 seconds.

For some applications, the duration of the total period is at least 24 hours.

For some applications, positioning the oral pressure probe in the air communication with the mouth includes positioning the oral pressure probe outside the mouth in the air communication with the mouth.

For some applications, activating the one or more processors includes activating the one or more processors to:
separately sense body posture and head posture, using a posture sensor, and
calculate each of the orally-weighted laterality-indices of each of the sub-periods partially in response to the sensed body posture and the sensed head posture such that each of the sub-periods is associated with a given combination of the sensed body posture and head posture.

For some applications, activating the one or more processors includes activating the one or more processors to transmit wireless signals indicative of the left-nostril, the right-nostril, and the oral airflows.

For some applications, activating the one or more processors includes activating the one or more processors to transmit wireless signals indicative of the series of orally-weighted laterality-indices.

For some applications, activating the one or more processors includes activating the one or more processors to calculate each of the laterality indices of each of the sub-periods by dividing (a) a difference between the left-nostril airflow and the right-nostril airflow over the sub-period by (b) a sum of the left-nostril airflow and the right-nostril airflow over the sub-period.

For some applications, activating the one or more processors includes activating the one or more processors to weight each of the orally-weighted laterality-indices of each of the sub-periods by multiplying (a) the laterality index by (b) (i) a difference between 1 and an absolute value of the normalized oral airflow over the sub-period (ii) raised to a power less than 1. For some applications, the power is no more than 0.5. For some applications, the power equals 0.25.

For some applications:
the method further includes coupling a housing to skin of a nape of a subject such that at least one position sensor within the housing is positioned over one or more of a first cervical vertebra (C1), a second cervical vertebra (C2), a third cervical vertebra (C3), and a fourth cervical vertebra (C4) of the subject, without being positioned over any vertebrae below the C4 vertebra, wherein the at least one position sensor is configured to sense a position of the position sensor and provide position-sensor outputs, and
activating the one or more processors includes activating the one or more processors to (a) ascertain, using the position-sensor outputs when the housing is coupled to the skin of the nape, body posture of the subject and, separately, head posture of the subject, and (b) generate one or more posture outputs indicative of the body posture and the head posture.

There is still further provided, in accordance with an application of the present invention, apparatus including:
a housing, configured to be coupled to skin of a nape of a subject;
exactly one position sensor, which (a) is configured to sense a position of the position sensor with at least three degrees of freedom and provide at least three position-sensor outputs, and (b) is disposed within the housing; and
one or more processors, which are configured to:
ascertain, using the position-sensor outputs when the housing is coupled to the skin of the nape, body posture of the subject and, separately, head posture of the subject, and
generate one or more posture outputs indicative of the body posture and the head posture.

For some applications, the exactly one position sensor is configured to sense the position of the position sensor with six degrees of freedom, and the at least three position-sensor outputs include six-dimensional rotational and acceleration outputs.

For some applications, the one or more processors are configured to:
based on the body posture and the head posture, select a combined posture of the subject from a plurality of predetermined possible combined postures that reflect both the body posture and the head posture, and
generate, as the one or more posture outputs, an output indicative of the combined posture of the subject.

For some applications, the one or more processors are configured such that the plurality of predetermined possible combined postures includes: upright, lying with a face facing left, and lying with the face facing right.

For some applications, the one or more processors are configured such that the plurality of predetermined possible combined postures further includes: lying on a left side, lying on a right side, lying on a stomach with a face facing down, lying on the stomach with the face facing left, lying on the stomach with the face facing right, lying on a back with the face facing up, lying on the back with the face facing left, and lying on back with the face facing right.

For some applications, the housing includes one or more flexible portions that allow conformance of the housing to the nape.

For some applications, the apparatus further includes a printed circuit board (PCB), which includes at least a portion of the one or more processors, and the PCB includes one or more flexible portions that allow conformance of the PCB to the nape.

There is additionally provided, in accordance with an application of the present invention, apparatus including:
- a housing, configured to be coupled to skin of a nape of a subject;
- at least one position sensor, which is configured to sense a position of the position sensor and provide position-sensor outputs, and is disposed within the housing; and
- one or more processors, which are configured to:
  - ascertain, using the position-sensor outputs when the housing is coupled to the skin of the nape, body posture of the subject and, separately, head posture of the subject,
  - based on the body posture and the head posture, select a combined posture of the subject from a plurality of predetermined possible combined postures that reflect both the body posture and the head posture, wherein the one or more processors are configured such that the plurality of predetermined possible combined postures includes: upright, lying with a face facing left, and lying with the face facing right, and
  - generate a posture output indicative of the combined posture of the subject.

For some applications, the one or more processors are configured such that the plurality of predetermined possible combined postures further includes: lying on a left side, lying on a right side, lying on a stomach with a face facing down, lying on the stomach with the face facing left, lying on the stomach with the face facing right, lying on a back with the face facing up, lying on the back with the face facing left, and lying on back with the face facing right.

For some applications:
- the apparatus includes exactly one position sensor, which is configured to sense the position of the position sensor with at least three degrees of freedom and provide at least three position-sensor outputs, and
- the one or more processors are configured to ascertain, using the position-sensor outputs when the housing is coupled to the skin of the nape, the body posture and, separately, the head posture.

For some applications, the exactly one position sensor is configured to sense the position of the position sensor with six degrees of freedom, and the at least three position-sensor outputs include six-dimensional rotational and acceleration outputs.

There is yet additionally provided, in accordance with an application of the present invention, a method including:
- coupling a housing to skin of a nape of a subject such that at least one position sensor within the housing is positioned over one or more of a first cervical vertebra (C1), a second cervical vertebra (C2), a third cervical vertebra (C3), and a fourth cervical vertebra (C4) of the subject, without being positioned over any vertebrae below the C4 vertebra, wherein the at least one position sensor is configured to sense a position of the position sensor and provide position-sensor outputs; and
- activating one or more processors to (a) ascertain, using the position-sensor outputs when the housing is coupled to the skin of the nape, body posture of the subject and, separately, head posture of the subject, and (b) generate one or more posture outputs indicative of the body posture and the head posture.

For some applications, coupling the housing to the skin of the nape includes:
- bending, by the subject, his or her head backward to identify a neck-rotation location along the nape, and
- coupling the housing to the skin of the nape such that the at least one position sensor within the housing is positioned over the identified neck-rotation location.

For some applications:
- exactly one position sensor is within the housing,
- the exactly one position sensor is configured to sense the position of the position sensor with at least three degrees of freedom and provide at least three position-sensor outputs,
- coupling the housing to the skin of the nape includes coupling the housing to the skin of the nape such that the exactly one position sensor within the housing is positioned over one or more of the C1, the C2, the C3, and the C4 vertebrae, without being positioned over any vertebrae below the C4 vertebra, and
- activating the one or more processors includes activating the one or more processors to ascertain, using the position-sensor outputs when the housing is coupled to the skin of the nape, the body posture and, separately, the head posture.

For some applications, activating the one or more processors includes activating the one or more processors to:
- based on the body posture and the head posture, select a combined posture of the subject from a plurality of predetermined possible combined postures that reflect both the body posture and the head posture, and
- generate, as the one or more posture outputs, a posture output indicative of the combined posture of the subject.

For some applications, activating the one or more processors includes activating the one or more processors such that the plurality of predetermined possible combined postures includes: upright, lying with a face facing left, and lying with the face facing right.

For some applications, activating the one or more processors includes activating the one or more processors such that the plurality of predetermined possible combined postures includes: lying on a left side, lying on a right side, lying on a stomach with a face facing down, lying on the stomach with the face facing left, lying on the stomach with the face facing right, lying on a back with the face facing up, lying on the back with the face facing left, and lying on back with the face facing right.

For some applications, activating the one or more processors includes activating the one or more processors to:
- based on the body posture and the head posture, select a combined posture of the subject from a plurality of predetermined possible combined postures that reflect both the body posture and the head posture, wherein the one or more processors is configured such that the plurality of predetermined possible combined postures includes: upright, lying with a face facing left, and lying with the face facing right, and
- generate, as the one or more posture outputs, a posture output indicative of the combined posture of the subject.

For some applications, activating the one or more processors includes activating the one or more processors such that the plurality of predetermined possible combined postures further includes: lying on a left side, lying on a right side, lying on a stomach with a face facing down, lying on the stomach with the face facing left, lying on the stomach with the face facing right, lying on a back with the face facing up, lying on the back with the face facing left, and lying on back with the face facing right.

There is also provided, in accordance with an application of the present invention, apparatus including a flow-through pressure probe, which includes:
- a baffle, which is shaped so as to define a concave chamber open on a first side for positioning in front of a mouth of a subject, the concave chamber shaped so to define one or more openings that pass entirely through a wall of the concave chamber to a second side of the concave chamber opposite the first side; and
- an oral-pressure tube in fluid communication with the first side of the concave chamber, such that a portion of airflow from the mouth passes into the oral-pressure tube when the baffle is positioned in front of the mouth.

For some applications, the wall of the concave chamber is shaped so as to define a mesh that defines the one or more openings.

For some applications, the one or more openings include between 5 and 128 openings.

For some applications, the one or more openings have an average cross-sectional area of between 0.5 and 20 mm2.

For some applications, the one or more openings have an aggregate cross-sectional area of between 50 and 70 mm2.

For some applications, the one or more openings have an average length of between 1 and 3.5 mm2.

For some applications, the first side of the baffle has a surface area, including the one or more openings, of between 800 and 1200 mm2.

For some applications, an aggregate cross-sectional area of the one or more openings is between 50% and 70% of a surface area of the first side of the baffle, including the one or more openings.

There is further provided, in accordance with an application of the present invention, a nasal-cycle measurement kit, including:
(a) a nostril-oral probe assembly, which includes:
  (i) a first left-nostril pressure probe, which is configured to be inserted into a left nostril of a subject, and includes a first left-nostril-pressure tube that is configured to transmit a first left-nostril pressure wave from the left nostril;
  (ii) a first right-nostril pressure probe, which is configured to be inserted into a right nostril of the subject, and includes a first right-nostril-pressure tube that is configured to transmit a first right-nostril pressure wave from the right nostril; and
  (iii) an oral pressure probe, which is configured to be positioned in air communication with a mouth of the subject, and includes an oral-pressure tube that is configured to transmit an oral pressure wave from the mouth; and
(b) a nostril probe assembly, which includes:
  (i) a second left-nostril pressure probe, which is configured to be inserted into the left nostril, and includes a second left-nostril-pressure tube that is configured to transmit a second left-nostril pressure wave from the left nostril; and
  (ii) a second right-nostril pressure probe, which is configured to be inserted into the right nostril, and includes a second right-nostril-pressure tube that is configured to transmit a second right-nostril pressure wave from the right nostril,
wherein the nostril probe assembly does not include an oral pressure probe.

For some applications:
the nasal-cycle measurement kit further includes a left-nostril pressure sensor, a right-nostril pressure sensor, and an oral pressure sensor,
the first left-nostril-pressure tube is configured, when coupled in fluid communication with the left-nostril pressure sensor, to transmit the first left-nostril pressure wave from the left nostril to the left-nostril pressure sensor,
the first right-nostril-pressure tube is configured, when coupled in fluid communication with the right-nostril pressure sensor, to transmit the first right-nostril pressure wave from the right nostril to the right-nostril pressure sensor,
the oral-pressure tube is configured, when coupled in fluid communication to with the oral pressure sensor, to transmit the oral pressure wave from the mouth to the oral pressure sensor,
the second left-nostril-pressure tube is configured, when coupled in fluid communication with the left-nostril pressure sensor, to transmit the second left-nostril pressure wave from the left nostril to the left-nostril pressure sensor, and
the second right-nostril-pressure tube is configured, when coupled in fluid communication with the right-nostril pressure sensor, to transmit the second right-nostril pressure wave from the right nostril to the right-nostril pressure sensor.

The present invention will be more fully understood from the following detailed description of embodiments thereof, taken together with the drawings, in which:

BRIEF DESCRIPTION OF THE DRAWINGS

FIG. 2 is a schematic illustration of a nasal-cycle measurement system, in accordance with an application of the present invention;

FIGS. 11A and 11B are schematic illustrations of a calibration wand for performing a calibration procedure, in accordance with an application of the present invention.

DETAILED DESCRIPTION OF APPLICATIONS

Figure 1A:
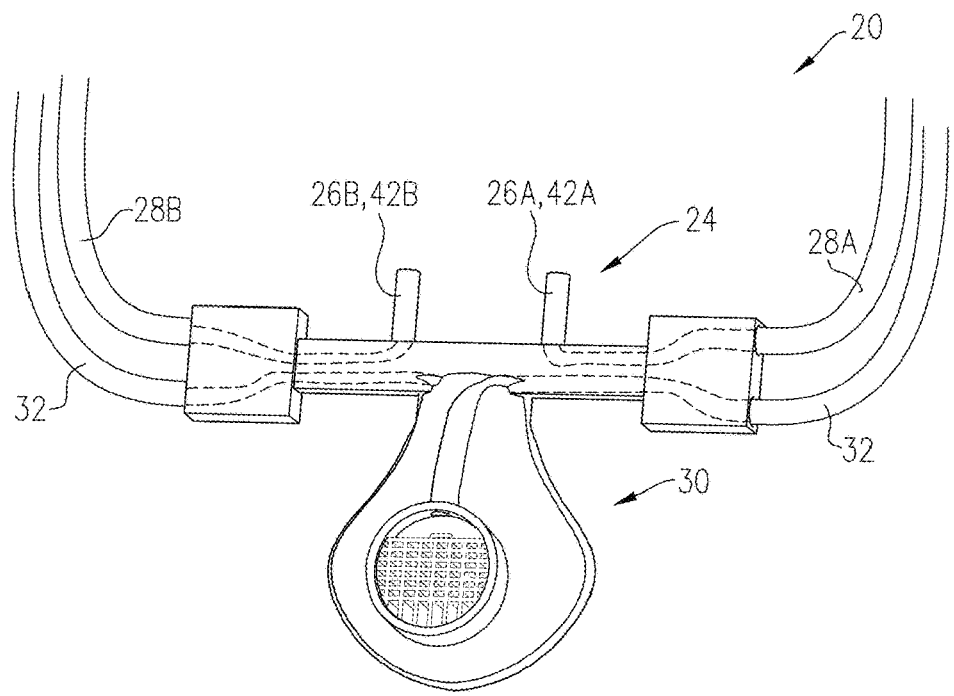
FIGS. 1A-B are schematic illustrations of a nasal-cycle measurement device, in accordance with an application of the present invention.
Figure 1B:
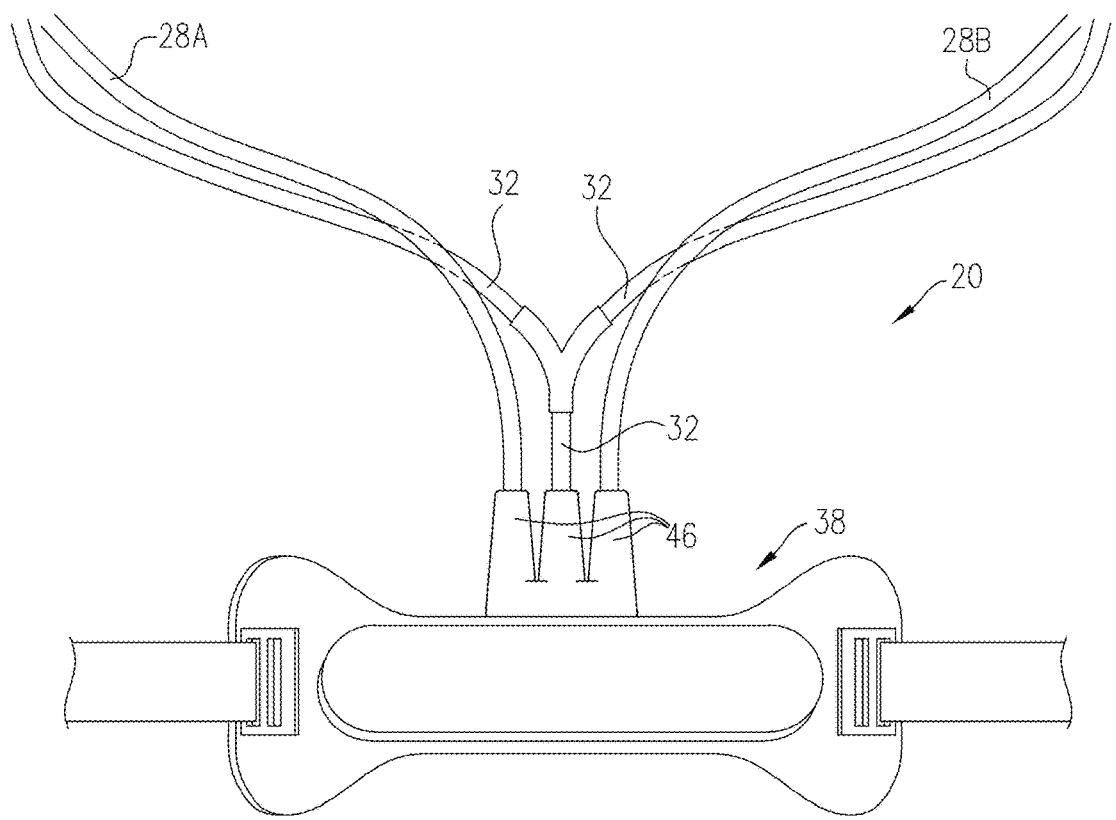

FIGS. 1A-B are schematic illustrations of a nasal-cycle measurement device 20, in accordance with an application of the present invention. Nasal-cycle measurement device 20 is configured to continuously measure and log upper airways airflow in the three upper airways: the left nostril, the right nostril, and the mouth, separately and simultaneously. Nasal-cycle measurement device 20 is typically configured to ascertain a nasal cycle, which is a measure of airflow asymmetry that may be indicative of balance in the autonomic nervous system. Device 20 is typically wearable.

Reference is also made to FIG. 2, which is a schematic illustration of a nasal-cycle measurement system 10, in accordance with an application of the present invention. FIG. 2 also shows a housing 38 of nasal-cycle measurement device 20 and components thereof.

For some applications, nasal-cycle measurement device 20 comprises:
- a left-nostril pressure sensor 22A, a right-nostril pressure sensor 22B, and an oral pressure sensor 23;
- a nostril-oral probe assembly 24;
- a memory 34; and
- a processor 36.

Nostril-oral probe assembly 24 comprises:
- a left-nostril pressure probe 26A, which is configured to be inserted into a left nostril of a subject, and comprises a left-nostril-pressure tube 28A that is configured to transmit a left-nostril pressure wave from the left nostril to left-nostril pressure sensor 22A;
- a right-nostril pressure probe 26B, which is configured to be inserted into a right nostril of the subject, and comprises a right-nostril-pressure tube 28B that is configured to transmit a right-nostril pressure wave from the right nostril to right-nostril pressure sensor 22B; and
- an oral pressure probe 30, which is configured to be positioned in air communication with a mouth of the subject, and comprises an oral-pressure tube 32 that is configured to transmit an oral pressure wave from the mouth to oral pressure sensor 23.

For some applications, nasal-cycle measurement device 20 comprises housing 38, which contains one or more of left-nostril pressure sensor 22A, right-nostril pressure sensor 22B, oral pressure sensor 23, memory 34, and processor 36, optionally as well as other components. To this end, housing 38 typically further comprises three pneumatic connectors 46, which are configured to be coupled in fluid communication with left-nostril-pressure tube 28A, right-nostril-pressure tube 28B, and oral-pressure tube 32, respectively. Typically, housing 38 is configured to be coupled to skin of a nape of a subject, such as described hereinbelow with reference to FIGS. 5A-B. Alternatively, one or more of the above-mentioned elements are not contained within the housing.

Typically, left-nostril, right-nostril, and oral pressure sensors 22A, 22B, and 23 sense pressure (indicative of resistance), which processor 36 (and/or processor 14, described hereinbelow) computationally converts to respective left-nostril, right-nostril, and oral airflows. Typically, when performing these conversions, the one or more processors use calibration data, such as described hereinbelow with reference to FIGS. 1A-5B. Optionally, the calculated airflows are stored in memory 34.

For some applications, left-nostril pressure sensor 22A, right-nostril pressure sensor 22B, and oral pressure sensor 23 comprise respective differential pressure sensors. For example, the sensors may be open to the environment at the sensor end, within the pneumatic connectors that link the probe to housing 38. Alternatively, oral pressure sensor 23 may be open to the environment at oral pressure probe 30, such as described hereinbelow with reference to FIGS. 7A-B.

For some applications, left-nostril and right-nostril pressure probes 26A and 26B comprise respective left-nostril and right-nostril tubes 42A and 42B, which are configured to be inserted into left and right nostrils of a human subject. Typically, left-nostril and right-nostril tubes 42A and 42B have outer diameters of at least 1 mm, no more than 4 mm, and/or between 1 and 4 mm, and/or inner diameters of at least 0.5 mm, no more than 3 mm, and/or between 0.5 and 3 mm; the narrowness of these tubes allows relatively comfortable wearing of nasal-cycle measurement device 20 over the 24 hours typically required to measure the nasal cycle.

Optionally, as shown, oral pressure probe 30 comprises two oral-pressure tubes 32 that are configured to transmit the oral pressure wave from the mouth to oral pressure sensor 23. The two tubes combine into one tube before fluid connection with oral pressure sensor 23. Providing two oral-pressure tubes 32 may provide greater volume, which may increase the sensitivity of measurement, particularly in configurations in which oral pressure probe 30 is configured to be positioned outside the mouth, such as described hereinbelow. Alternatively, oral pressure probe 30 comprises a single oral-pressure tube 32 (configuration not shown).

Memory 34 is configured to store left-nostril, right-nostril, and oral pressures sensed by left-nostril, right-nostril, and oral pressure sensors 22A, 22B, and 23, respectively, over a total period having a duration of at least 12 hours, typically at least 24 hours. For some applications in which the total period is less than 24 hours, nasal-cycle measurement device 20 is configured to sense and store the pressures only while the subject is asleep, or only while the subject is awake. For example, memory 34 may record at between 6 and 200 Hz.

Typically, nasal-cycle measurement system 10 further comprises an external computer 12, which comprises one or more processors 14 and a memory 16. For example, external computer 12 may comprise a smartphone, a personal computer, a tablet, or any other computing device. Optionally, external computer 12 is configured to transmit output over the internet or another private or public network, as is known in the art. Typically, external computer 12 comprises one or more wireless interfaces 18, e.g., a receiver/transmitter, which may, for example, implement Bluetooth. External computer 12 may implement the functions thereof described herein in hardware and/or software.

Figure 4:
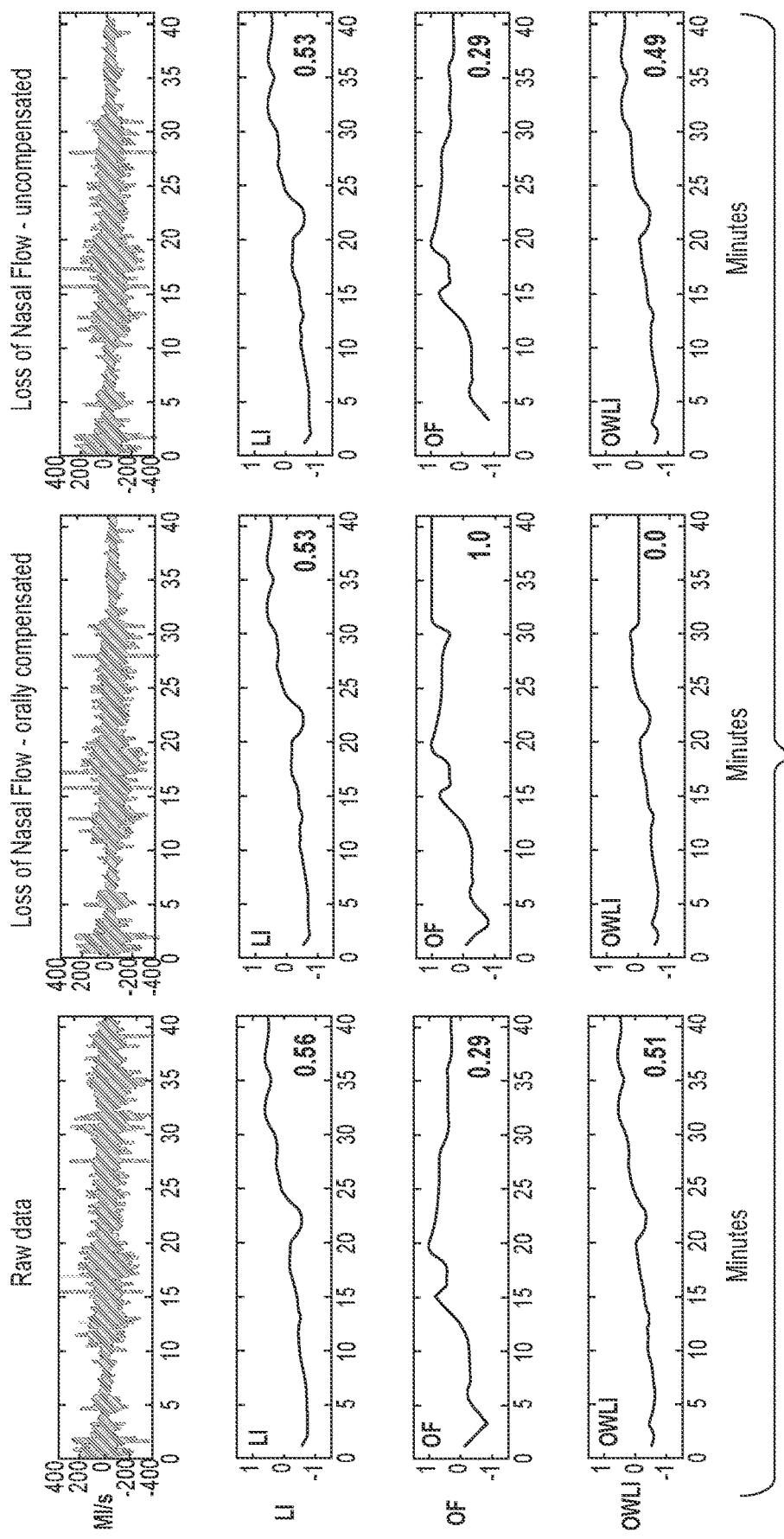
FIG. 4 includes several graphs of exemplary calculations made by the nasal-cycle measurement system of FIG. 2, in accordance with an application of the present invention.

Reference is now made to FIG. 4, which includes several graphs of exemplary calculations made by nasal-cycle measurement system 10, in accordance with an application of the present invention. For example, external computer 12 may generate these outputs. For some applications, the one or more of processors 14 and/or 36 are configured to calculate, based on the left-nostril, the right-nostril, and the oral airflows, a series of orally-weighted laterality-indices (OWLIs) over a respective series of sub-periods of the total period. This calculation, as well as the other calculations described herein, may be performed: entirely by the one or more of processors 14 of external computer 12; entirely by processor 36 of nasal-cycle measurement device 20 and/or by processor 66, if provided, as described hereinbelow; partially by the one or more of processors 14 of external computer 12 and partially by processor 36 and/or 66; and/or entirely or partially by another processor, such as a remote processor of a server connected to a private or public network, such as the Internet.

Each of the orally-weighted laterality-indices (OWLIs) of each of the sub-periods is indicative of a laterality index (LI) over the sub-period weighted by a normalized oral airflow over the sub-period, such that the greater the normalized oral airflow, the smaller the orally-weighted laterality-index (OWLI). Each of the laterality indices (LIs) of each of the sub-periods reflects relative airflow through the left and the right nostrils over the sub-period. For example, a value of 1 may represent airflow only through right nostril 50B, a value of −1 may represent airflow only through left nostril 50A, and a value of 0 may represent equal flow through left and right nostrils 50A and 50B. For example, oral airflow may be normalized to range from −1 to 1.

Each of the orally-weighted laterality-indices (OWLIs) of each of the sub-periods reflects oral-flow-weighted relative airflow through the left and the right nostrils over the sub-period. For example, each of the sub-periods may have a duration of between 30 and 180 seconds, such as between 45 and 120 seconds, e.g., 60 seconds.

For some applications, the one or more of processors and/or 36 are configured to calculate an overall laterality index equal to an average of the orally-weighted laterality-indices (OWLIs) during the total period, or an average of respective absolute values of the OWLIs during the total period. The overall laterality index is a measure of the subject's nasal cycle, typically including a measure of autonomic tone/balance derived from relative left/right nasal measured airflows. Typically, the overall orally-weighted laterality index is a single value measure of the nasal cycle.

For some applications, the one or more of processors 14 and/or 36 are configured to calculate each of the laterality indices (LIs) of each of the sub-periods by dividing (a) a difference between the left-nostril airflow and the right-nostril airflow over the sub-period by (b) a sum of the left-nostril airflow and the right-nostril airflow over the sub-period, for example using the following Equation 1:

$$LI = \frac{(Flow_R - Flow_L)}{(Flow_R + Flow_L)} \quad \text{(Equation 1)}$$

For some applications, the one or more of processors 14 and/or 36 are configured to weight each of the orally-weighted laterality-indices (OWLIs) of each of the sub-periods by multiplying (a) the laterality index (LI) by (b) (i) a difference between 1 and an absolute value of the normalized oral airflow over the sub-period (ii) raised to a power less than 1, e.g., a power no more than 0.5, such as 0.25, for example using the following Equation 2:

$$OWLI = LI \ast ((1-abs(OF))^{0.25}) \quad \text{(Equation 2)}$$

Although typically reciprocal, each nostril can also cycle independently, and both nostrils can shift to the closed state, thus forcing mouth-breathing. This can happen mostly at night. Without the oral-weighting techniques described herein, a "zero signal" measured in both nostrils can indicate either that both nostrils have closed and the person is mouth-breathing, or that the person is in a state of apnea, not breathing at all. The oral-weighting techniques described herein allow discrimination between these two states. As can be seen in FIG. 4, when normalized oral airflow is large (close to 1 in absolute value), OWLI is smaller, and conversely, when the absolute value of the normalized oral airflow is smaller, the OWLI is larger, i.e., more meaningful. This allows for faithful nasal cycle characterization.

Reference is still made to FIG. 4. The top row three panels are a 45-minute raw recording of left and right nostril airflows. In the left top panel, the data is unmodified, but in the middle and right panels a loss of nasal airflow is simulated at the end of the recording. The difference between the middle and right panels is that in the middle, the loss in nasal airflow was compensated for by an increase in oral airflow (OF). In other words, there was a shift from nasal to oral airflow. In the right panels, the loss in nasal airflow is not compensated for. In other words, there is a reduction in total airflow (e.g., apnea).

If the laterality index (LI) were to be computed using just left and right nostril recordings, the LI at the end of the recording would be the same in the middle and right panels (LI=0.53). In other words, whether airflow shifted from nose to mouth, or in turn stopped altogether, LI would remain the same. Without the use of the weighting techniques described herein, it would be impossible to discriminate between these two dramatically different states. By contrast, in the middle panel with oral compensation, OWLI is now 0.0, yet in the right panel without oral compensation (i.e., with apnea), OWLI is now 0.48. Thus, OWLI provides a faithful measure of the nasal cycle.

For some applications, oral pressure probe 30 is configured to be positioned outside the mouth (typically in front of the mouth) in the air communication with the mouth, optionally as described in more detail hereinbelow with reference to FIGS. 7A-B.

Reference is again made to FIG. 2. For some applications, nasal-cycle measurement device 20 is configured to also continuously sense and log both body and head posture. To this end, nasal-cycle measurement device 20 comprises a posture-sensing unit 40 that is configured to separately sense body posture and head posture. The one or more of processors 14 and/or 36 are configured to calculate each of the orally-weighted laterality-indices of each of the sub-periods partially in response to the sensed body posture and the sensed head posture such that each of the sub-periods is associated with a given combination of the sensed body posture and head posture.

For some applications, nasal-cycle measurement device (such as housing 38 thereof) further comprises a wireless transmitter 44, which is configured to transmit:
  wireless signals indicative of the left-nostril, the right-nostril, and the oral pressures and/or airflows,
  wireless signals indicative of the series of orally-weighted laterality-indices,
  a wireless signal indicative of the overall orally-weighted laterality index (OWLI), and/or
  wireless signals indicative of any other intermediary calculations by processor 36.

Wireless transmitter 44 may transmit to one or more of the one or more wireless interfaces 18 of external computer 12, and/or to any other external device.

For example, wireless transmitter 44 may implement Bluetooth technology.

For some applications, nasal-cycle measurement device further comprises one or more batteries 45, e.g., rechargeable batteries.

For some applications, housing 38 further comprises one or more user outputs 47, such as visual and/or audio outputs, e.g., one or more LEDs or buzzers. For example, user outputs 47 may:

alert the user to certain respiratory patterns, provide an indication of battery charge level, provide a device identifier (such as when more than one device is in a room, and it is desired to link the devices), provide a visual indicator of respiration; for example, one of the LEDs may flicker at the speed of respiration, and/or provide a visual indicator of the laterality index (LI); for example, the colors emitted by the LEDs may be set to indicate which nostril is open.

Alternatively or additionally, user outputs 47 may provide feedback to the user in order to encourage particular flow patterns, e.g., increased flow through the left or the right nostril. A user who is in a state of right-nostril dominance (associated with sympathetic dominance, or stress) may wish to shift to left-nostril dominance (associated with parasympathetic dominance, or calm). The device may provide the user with a visual indication (by the LEDs or on the screen of a device such as cell phone) of the trending shift in LI, as a biofeedback signal for shifting nostril dominance.

For some applications, housing 38 further comprises an electrical connector 48, e.g., a micro HDMI. For some applications, nasal-cycle measurement device 20 further comprises a docking station, to which housing 38 may be coupled via electrical connector 48. Typically, the docking station comprises battery charging circuits, and optionally a WIFI relay, which enables uploading recorded information from memory 34 and transmitting it via WIFI over the internet to a remote server for analysis.

Figure 3:
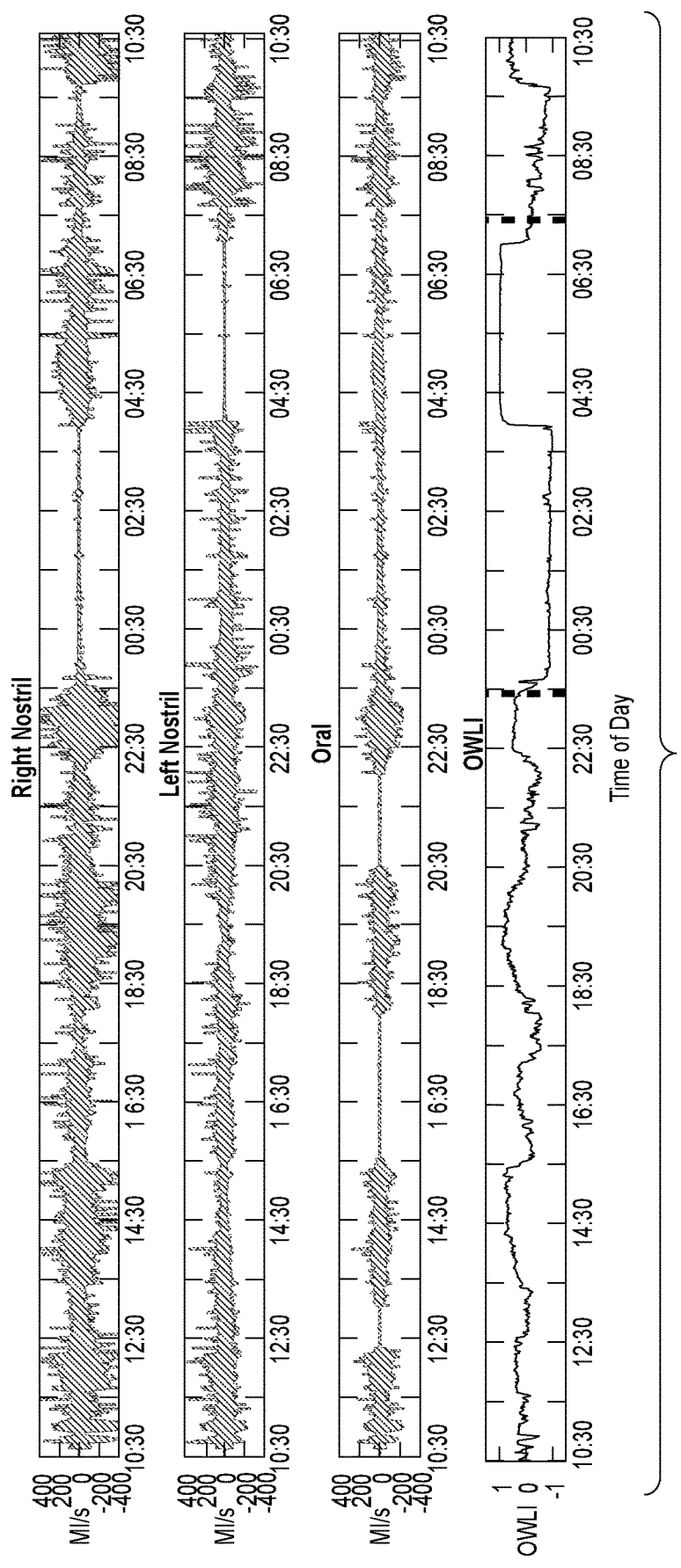
FIG. 3 includes several graphs of exemplary output of the nasal-cycle measurement system of FIG. 2, in accordance with an application of the present invention.

Reference is now made to FIG. 3, which includes several graphs of exemplary output of nasal-cycle measurement system 10, in accordance with an application of the present invention. For example, external computer 12 may generate these outputs. The outputs may include, for example:

left and right nostril airflow;

oral airflow;

the orally-weighted laterality-index (OWLI) described hereinabove with reference to FIGS. 1A-B and 2; and/or combined body/head posture, such as described hereinbelow with reference to FIG. 2.

The outputs may be generated in one or more data files and/or one or more charts, for example. The exemplary outputs shown in FIG. 3 reflect a 24-hour recording. The vertical dashed lines at 23:30 and 7:30 reflect nighttime sleep onset and termination, respectively.

Figure 5A:
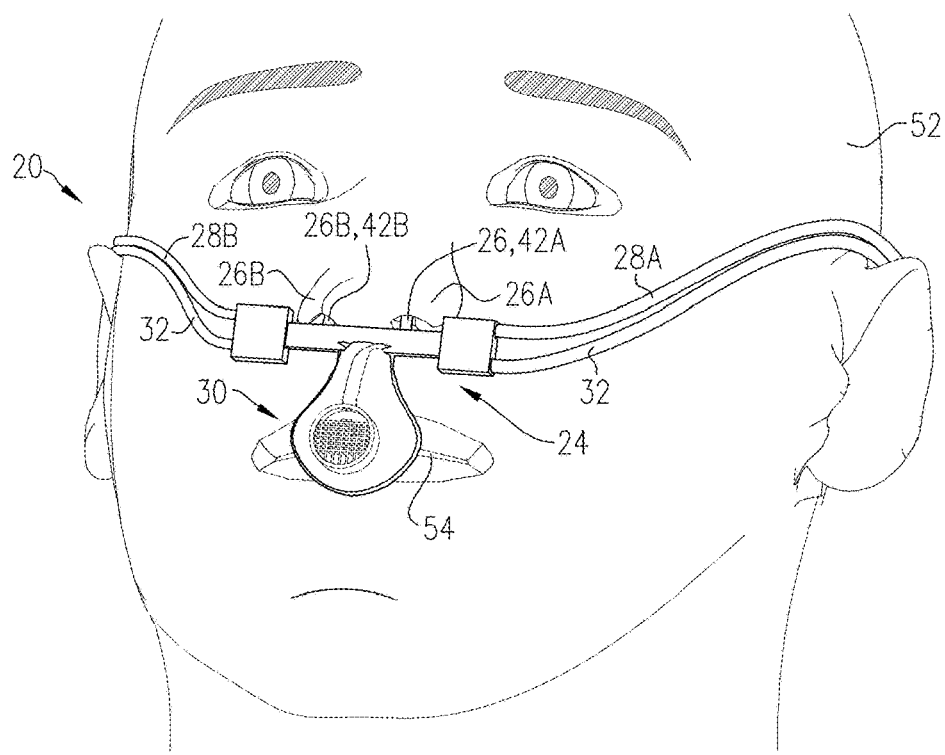
FIGS. 5A-B are schematic illustrations of the application of the nasal-cycle measurement device of FIGS. 1A-B to a human subject, in accordance with an application of the present invention.
Figure 5B:
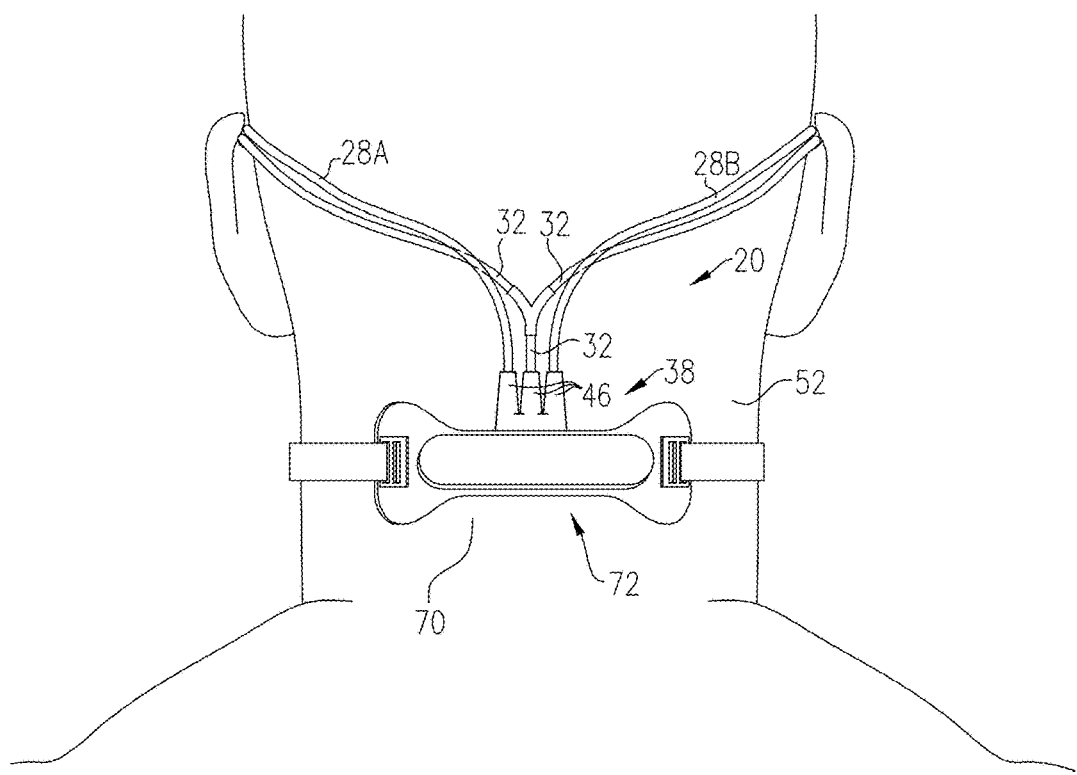

Reference is now made to FIGS. 5A-B, which are schematic illustrations of the application of nasal-cycle measurement device 20 to a human subject, in accordance with an application of the present invention.

In some applications, a method of using a method of using nasal-cycle measurement device 20 comprises:

inserting left-nostril pressure probe 26A into a left nostril 50A of a human subject 52, such that left-nostril-pressure tube 28A transmits the left-nostril pressure wave from left nostril 50A to left-nostril pressure sensor 22A;

inserting right-nostril pressure probe 26B into a right nostril 50B of subject 52, such that right-nostril-pressure tube 28B transmits the right-nostril pressure wave from right nostril 50B to right-nostril pressure sensor 22B;

positioning oral pressure probe 30 in air communication with a mouth 54 of subject 52 (typically outside mouth 54 in the air communication with mouth 54), such that oral-pressure tube 32 transmits the oral pressure wave from mouth 54 to oral pressure sensor 23; and activating nasal-cycle measurement device 20 to store the sensed pressures, over a total period having a duration of at least 12 hours, such as at least 24 hours, and calculate the series of orally-weighted laterality-indices (OWLIs), as described hereinabove with reference to FIGS. 1A-B, and, optionally, one or more of the other calculations described hereinabove with reference to FIGS. 1A-B.

Reference is again made to FIG. 2. In some applications of the present invention, nasal-cycle measurement device 20 comprises posture-sensing unit 40. Posture-sensing unit 40 may be integrated with other elements of nasal-cycle measurement device 20, such as illustrated, or may be implemented separately from other elements of nasal-cycle measurement device 20 (configuration not shown). Alternatively, posture-sensing unit 40 is provided entirely separately from nasal-cycle measurement device 20 and optionally used for applications unrelated to the nasal cycle.

It has been demonstrated that the nasal cycle shifts with body and/or head posture. Thus, simultaneously recording posture of both the body and the head may provide useful information in combination with the techniques described herein for nasal-cycle characterization. Body and head posture are mostly the same, accept in one yet critical phase: while sleeping, and primarily on the stomach, the head can turn either left, hence left nostril up, or right, hence right nostril up. This may represent important information for understanding shifts in the nasal cycle, so it may be useful to obtain and log this information.

Posture-sensing unit 40 comprises:

housing 38 (as shown), or another housing separate from housing 38 (configuration not shown), which is configured to be coupled to skin of a nape of subject 52;

at least one position sensor 64, which is configured to sense a position of position sensor 64 and provide position-sensor outputs, and which is disposed within housing 38; and a processor 66.

References hereinbelow to housing 38 of posture-sensing unit 40 are to be understood as also referring to the housing of posture-sensing unit 40 in configurations in which posture-sensing unit 40 comprises a separate housing from the housing described hereinabove with reference to FIGS. 1A-B and 2.

In configurations in which posture-sensing unit 40 is integrated with nasal-cycle measurement device 20, processor 36 of nasal-cycle measurement device 20 typically comprises processor 66, and housing 38 of nasal-cycle measurement device 20 also serves as the housing of posture-sensing unit 40.

For some applications, the at least one position sensor 64 of posture-sensing unit 40 comprises exactly one position sensor 64, which is configured to sense a position of position sensor 64 with at least three degrees of freedom and provide at least three position-sensor outputs. The one or more of processors 14 and/or 66 are configured to:

ascertain, using the position-sensor outputs when housing 38 is coupled to the skin of the nape, body posture of subject 52 and, separately, head posture of subject 52, and generate one or more posture outputs indicative of the body posture and the head posture.

For some applications, the exactly one position sensor 64 is configured to sense the position of position sensor 64 with six degrees of freedom, and the at least three position-sensor outputs include six-dimensional rotational and acceleration outputs.

For some applications, the at least one position sensor 64 of posture-sensing unit 40 is configured to sense a position of position sensor 64 and provide position-sensor outputs. The one or more of processors 14 and/or 66 are configured to:
- ascertain, using the position-sensor outputs when housing 38 is coupled to the skin of the nape, body posture of subject 52 and, separately, head posture of subject 52,
- based on the body posture and the head posture, select a combined posture of subject 52 from a plurality of predetermined possible combined postures that reflect both the body posture and the head posture, and
- generate a posture output indicative of the combined posture of subject 52.

For some applications, the one or more of processors 14 and/or 66 are configured such that the plurality of predetermined possible combined postures includes: upright, lying with a face facing left, and lying with the face facing right. The "upright" posture means a vertical position, either sitting or standing. The posture information may be useful because lying with the face facing left or right is associated with greater flow in the contralateral nostril, such as described in above-mentioned article by Kahana-Zweig R et al.

Optionally, the one or more of processors 14 and/or 66 are configured such that the plurality of predetermined possible combined postures further includes the following more specific postures for lying with the face facing left right, or neither left nor right: lying on a left side, lying on a right side, lying on a stomach (i.e., prone) with a face facing down, lying on the stomach with the face facing left, lying on the stomach with the face facing right, lying on a back (i.e., supine) with the face facing up, lying on the back with the face facing left, and lying on back with the face facing right.

For some applications, housing 38 comprises one or more flexible portions 76 that allow conformance of housing 38 to the nape, in order to allow comfortable wearing of the housing over the 24 hours typically required for measuring the nasal cycle. For some of these applications, posture-sensing unit 40 further comprises a printed circuit board (PCB) 78, which comprises at least a portion of processor 66. Typically, PCB 78 comprises one or more flexible portions 80 that allow conformance of PCB 78 to the nape, such as by allowing flexing around respective flex axes 81. Typically, housing 38 comprises an adhesive (e.g., double-sided medical adhesive tape) for coupling the housing to the nape of the neck; alternatively, housing 38 is coupled to the nape using other connecting techniques, such as straps.

Reference is again made to FIGS. 5A-B, which show the application of housing 38 to subject 52, in accordance with an application of the present invention. Housing 38 may contain elements of nasal-cycle measurement device 20 and/or of posture-sensing unit 40. In this configuration, housing 38 is coupled to skin 70 of a nape 72 of subject 52.

Figure 6:
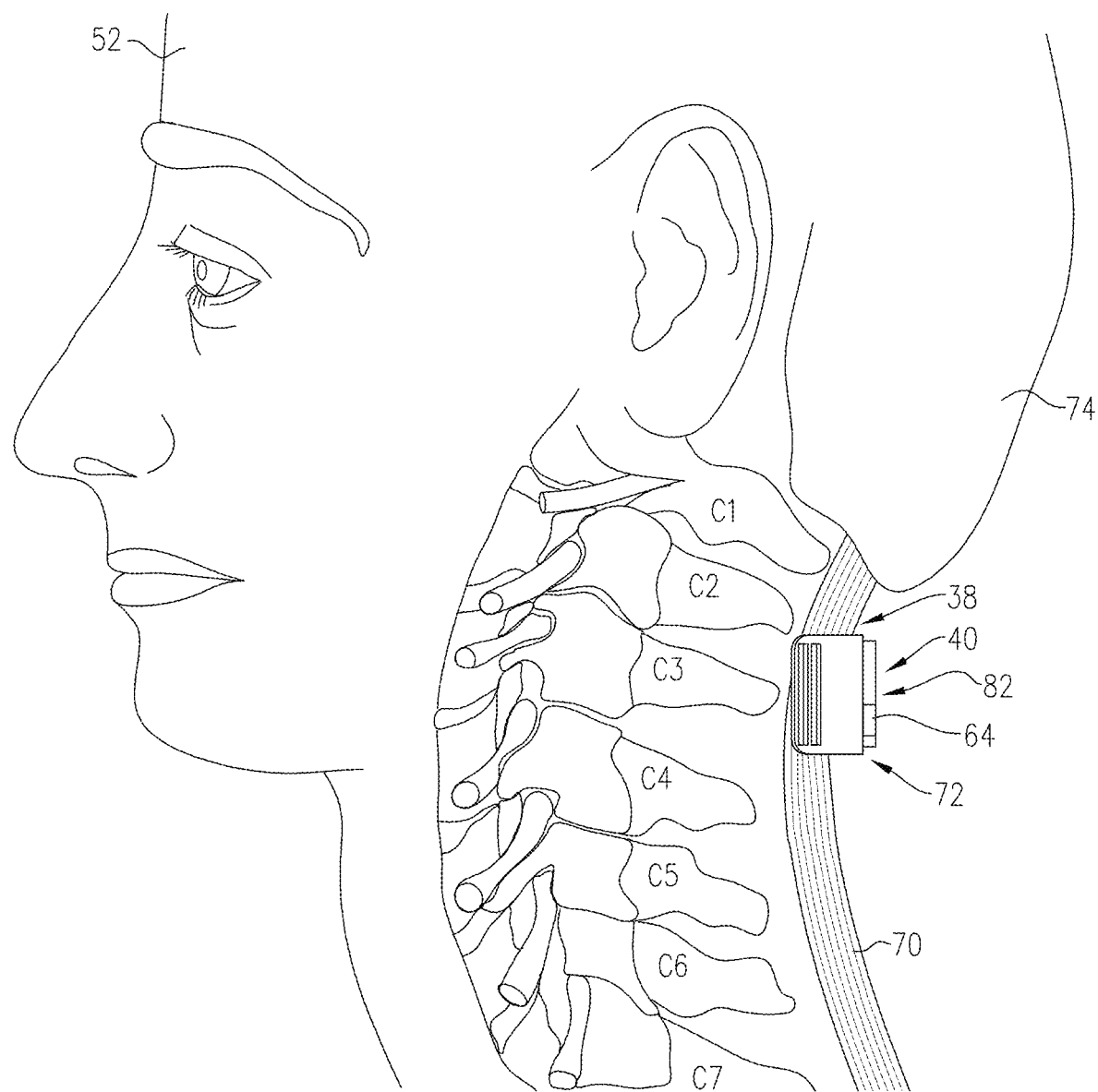
FIG. 6 is a schematic illustration of a housing of the nasal-cycle measurement device of FIGS. 1A-B coupled to skin of a nape, in accordance with an application of the present invention.

Reference is now made to FIG. 6, which is a schematic illustration of housing 38 coupled to skin 70 of nape 72, in accordance with an application of the present invention. For some applications in which housing 38 contains at least elements of posture-sensing unit 40, housing 38 is coupled to skin 70 of nape 72 of subject 52 such that at least one position sensor 64 within housing 38 is positioned over one or more of a first cervical vertebra (C1) (also known as Atlas), a second cervical vertebra (C2) (also known at Axis), a third cervical vertebra (C3), and a fourth cervical vertebra (C4) of subject 52 (typically over C2, C3, and/or C4), without being positioned over any vertebrae below the C4 vertebra.

Posture-sensing unit 40 may be activated to sense posture and generate one or more posture outputs as described hereinabove with reference to FIG. 2.

Reference is still made to FIG. 6. In an application of the present invention, a method is provided of coupling housing 38 to skin 70 of nape 72, the coupling method comprising:
- bending, by subject 52, his or her head 74 backward to identify a neck-rotation location 82 along nape 72, which typically corresponds to C2-C4, and
- coupling housing 38 to skin 70 of nape 72 such that the at least one position sensor 64 within housing 38 is positioned over the identified neck-rotation location 82.

For some applications, the at least one position sensor 64 comprises exactly one position sensor 64 within housing 38, and the exactly one position sensor 64 is configured to sense the position of position sensor 64 with at least three degrees of freedom and provide at least three position-sensor outputs. Housing 38 is coupled to skin 70 of nape 72 such that the exactly one position sensor 64 within housing 38 is positioned over one or more of the C1, the C2, the C3, and the C4 vertebrae, without being positioned over any vertebrae below the C4 vertebra. The one or more of processors 14 and/or 66 are activated to ascertain, using the position-sensor outputs when housing 38 is coupled to skin 70 of nape 72, the body posture and, separately, the head posture.

For some applications, the one or more of processors 14 and/or 66 are activated to:
- based on the body posture and the head posture, select a combined posture of subject 52 from a plurality of predetermined possible combined postures that reflect both the body posture and the head posture, and
- generate, as the one or more posture outputs, a posture output indicative of the combined posture of subject 52.

For some applications, the one or more of processors and/or 66 are activated such that the plurality of predetermined possible combined postures includes: upright, lying with a face facing left, and lying with the face facing right. For some of these applications, the one or more of processors 14 and/or 66 are activated such that the plurality of predetermined possible combined postures further includes: lying on a left side, lying on a right side, lying on a stomach with a face facing down, lying on the stomach with the face facing left, lying on the stomach with the face facing right, lying on a back with the face facing up, lying on the back with the face facing left, and lying on back with the face facing right.

For some applications, the one or more of processors 14 and/or 66 are activated to:
- based on the body posture and the head posture, select a combined posture of subject 52 from a plurality of predetermined possible combined postures that reflect both the body posture and the head posture, and
- generate, as the one or more posture outputs, a posture output indicative of the combined posture of subject 52.

Figure 8A:
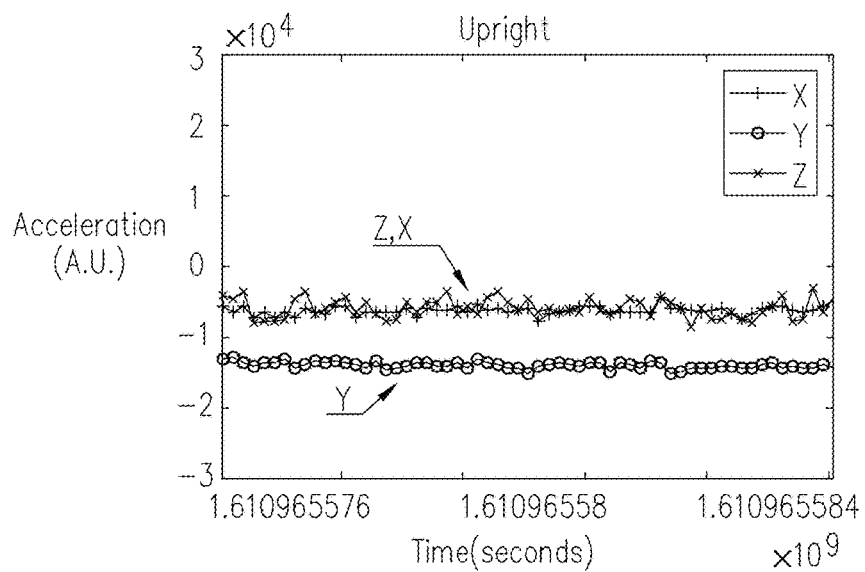
FIGS. 8A-I include graphs showing position sensor outputs, in accordance with an application of the present invention.
Figure 8B:
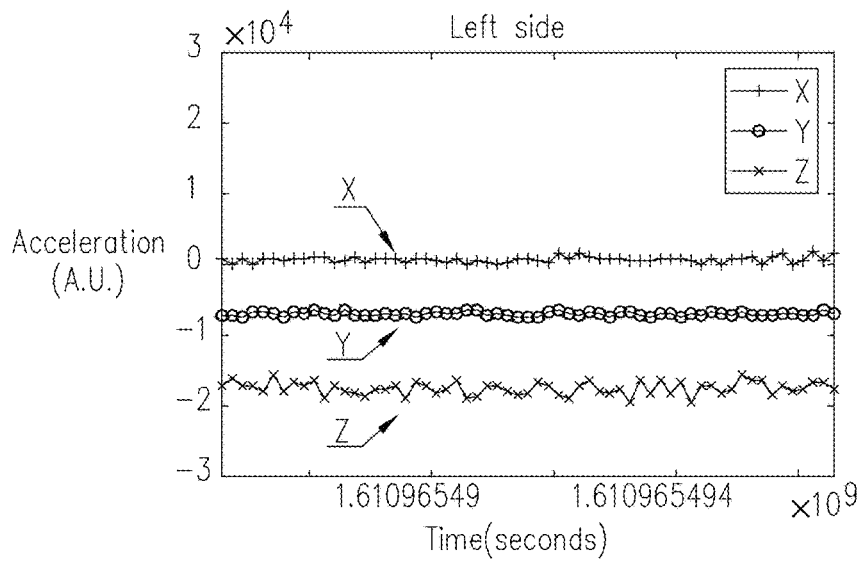
Figure 8C:
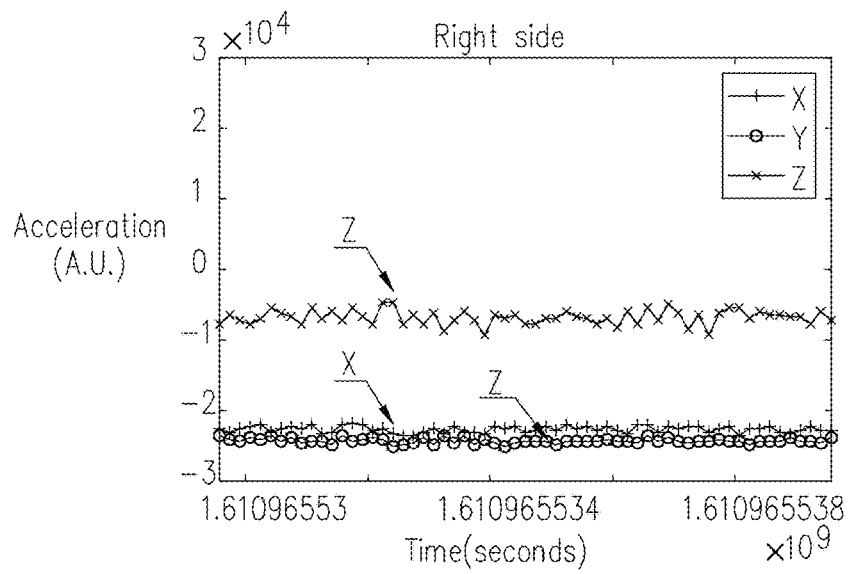
Figure 8D:
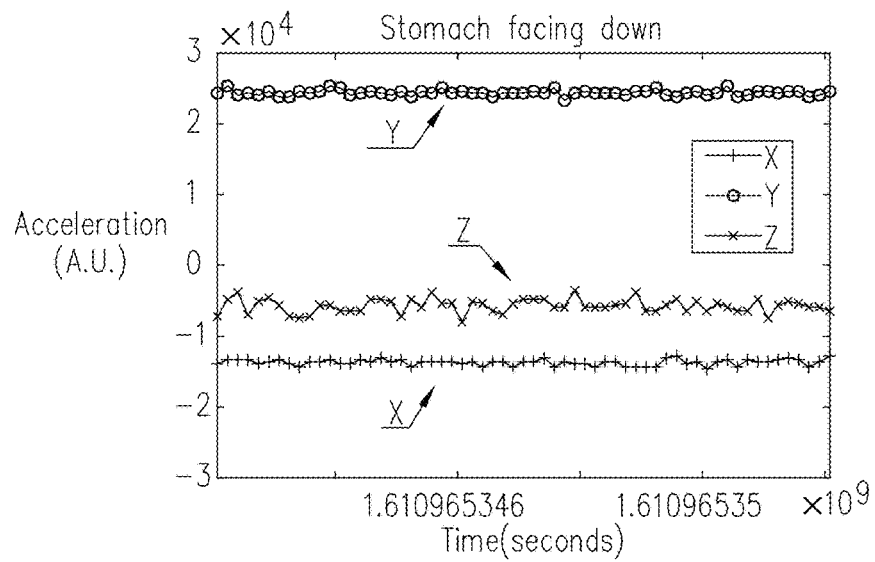
Figure 8E:
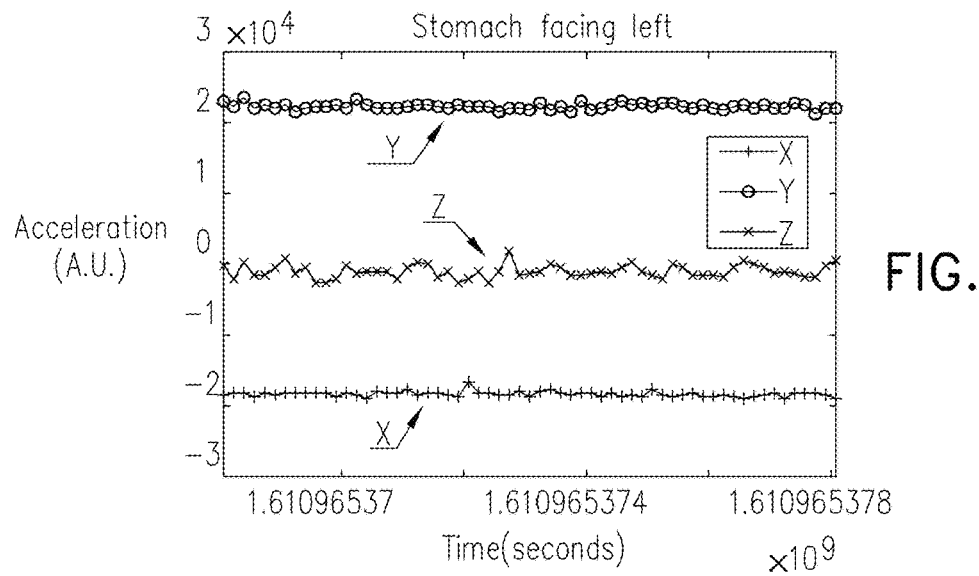
Figure 8F:
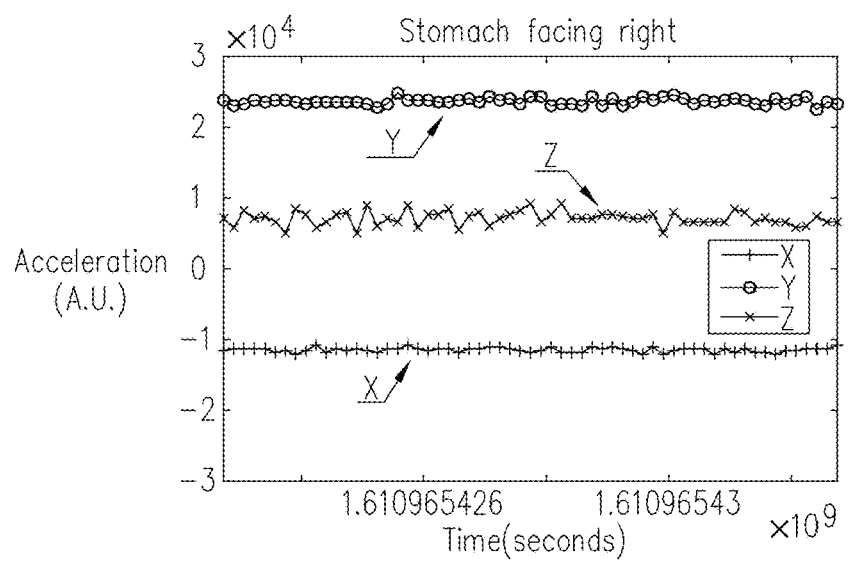
Figure 8G:
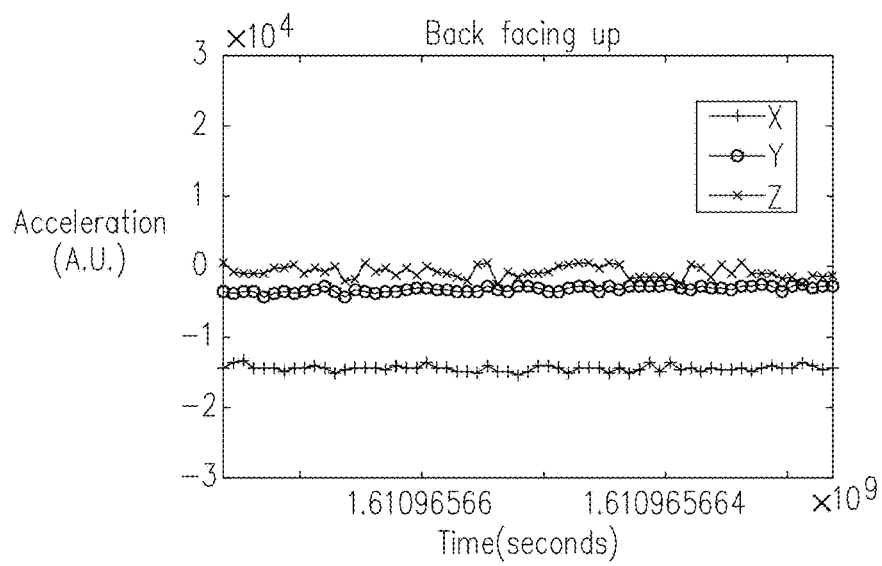
Figure 8H:
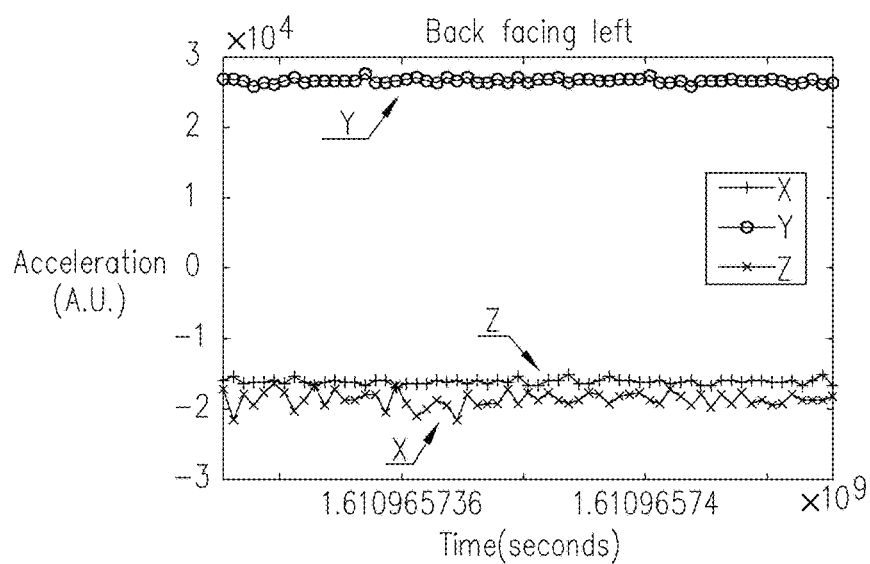
Figure 8I:
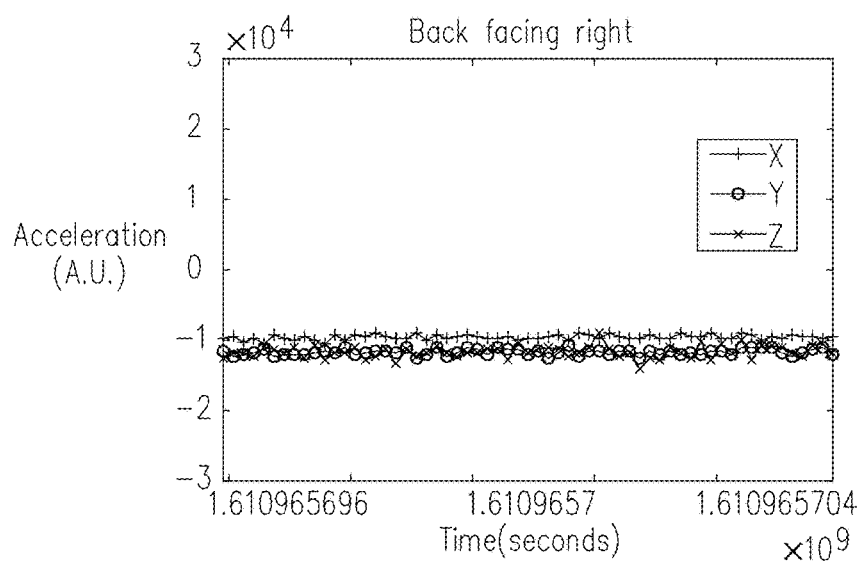

Reference is now made to FIGS. 8A-I, which include graphs showing position sensor outputs, in accordance with an application of the present invention. In an experiment conducted by the inventors, users wore a device similar to housing 38 comprising posture-sensing unit 40, with the housing coupled to skin of the nape of the subject such that at least one position sensor within the housing was positioned over the second cervical vertebra (C2), such as described hereinabove with reference to FIG. 6. Postures were sensed, using the techniques described hereinabove, with the user having nine different postures of interest:

1. upright, as shown in FIG. 8A;
2. lying on the left side, as shown in FIG. 8B;
3. lying on the right side, as shown in FIG. 8C;
4. lying on the stomach, facing down, as shown in FIG. 8D;
5. lying on the stomach, facing left, as shown in FIG. 8E;
6. lying on the stomach, facing right, as shown in FIG. 8F;
7. lying on back, facing up, as shown in FIG. 8G;
8. lying on the back, facing left, as shown in FIG. 8H; and
9. lying on the back, facing right, as shown in FIG. 8I. Using x, y, and z coordinates provided by the position sensor, 100% accuracy was achieved in classification of head and body posture into the nine above-mentioned categories, as shown in FIG. 8. As can be seen in the graphs, the device was able to independently ascertain, for supine subjects, whether their heads were facing left or right. This allows ascertaining which nostril was up and which was down.

Figure 9A:
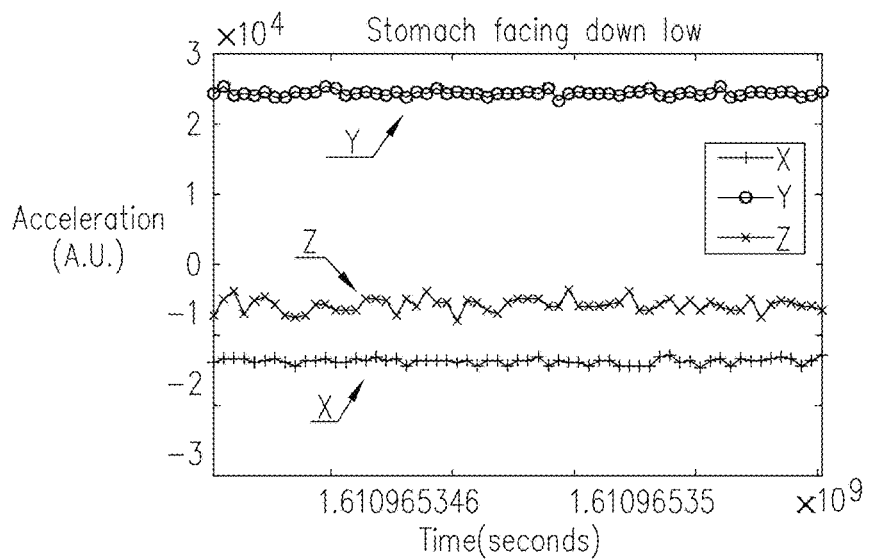
FIGS. 9A-C include graphs showing additional sensor outputs.
Figure 9B:
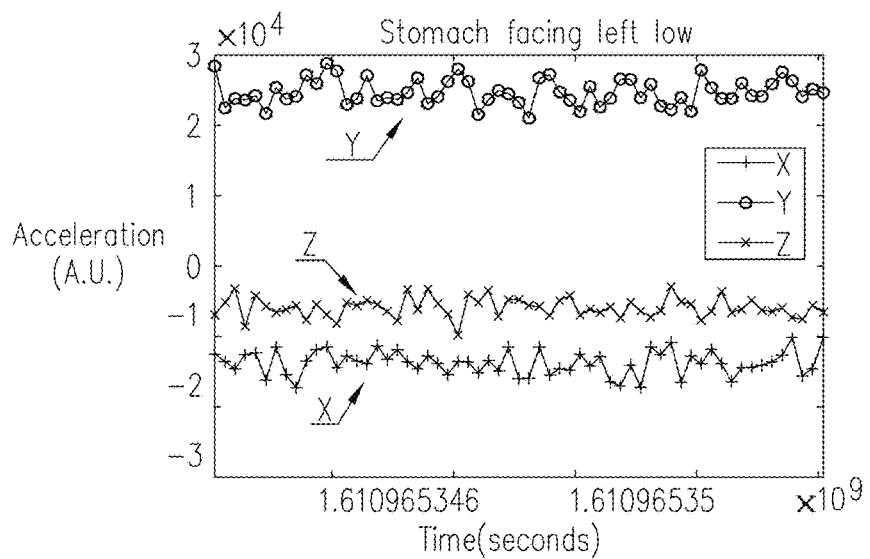
Figure 9C:
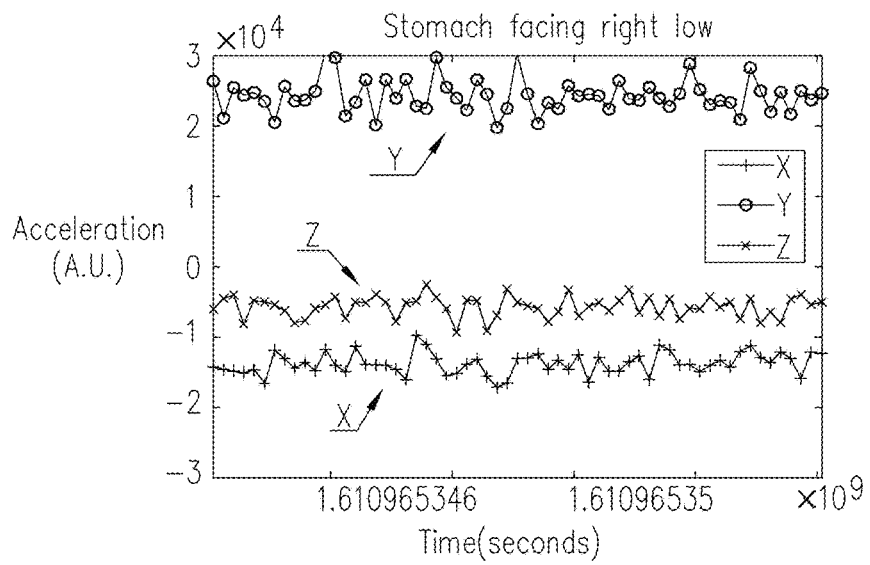

Reference is now made to FIGS. 9A-C, which include graphs showing position sensor outputs. In an experiment conducted by the inventors, users wore a device similar to housing 38 comprising posture-sensing unit 40, with the housing coupled to skin of the nape of the subject such that at least one position sensor within the housing was positioned significantly lower than C4, such that the housing was not positioned as described hereinabove with reference to FIG. 6. Postures were sensed, using the techniques described hereinabove, with the user having three different postures of interest:

1. lying on the stomach, facing down, as shown in FIG. 9A;
2. lying on the stomach, facing left, as shown in FIG. 9B; and
3. lying on the stomach, facing right, as shown in FIG. 9C.

As can be seen (particularly in comparison with the data shown in the graphs of FIGS. 8D-F), the data produced when the housing was positioned too low is inaccurate. This observation supports the importance of placement of the housing as described hereinabove with reference to FIG. 6.

Figure 7A:
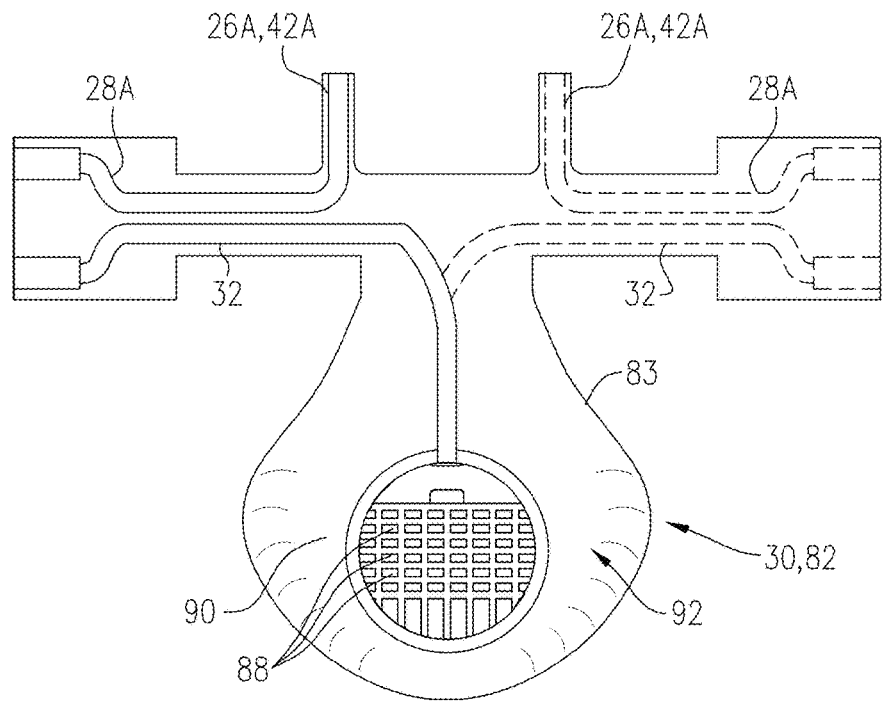
FIGS. 7A-B are schematic illustrations of one configuration of an oral pressure probe of the nasal-cycle measurement device of FIGS. 1A-B, in accordance with an application of the present invention.
Figure 7B:
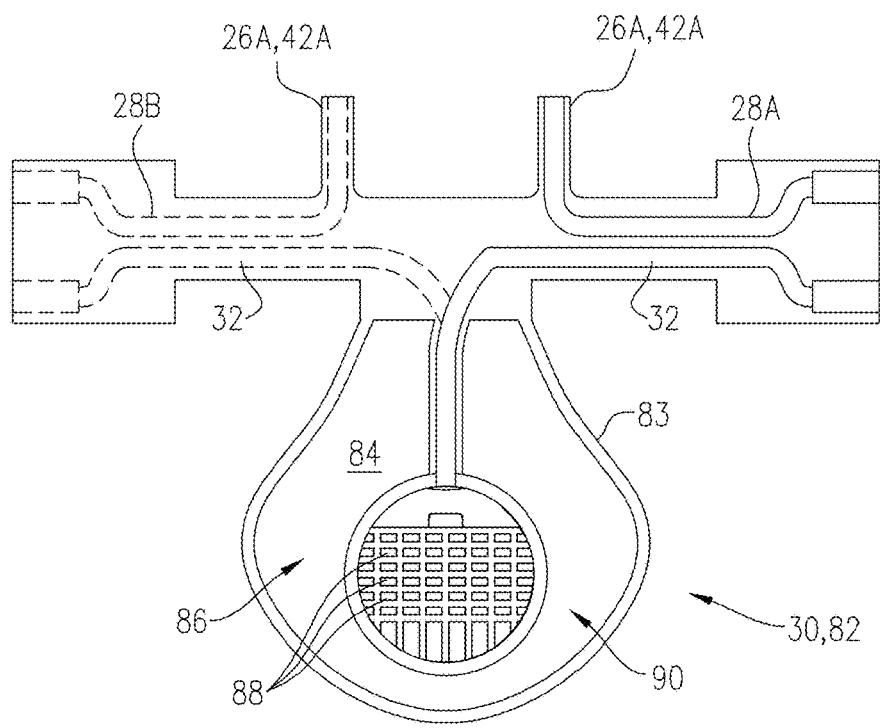

Reference is now made to FIGS. 7A-B, which are schematic illustrations of one configuration of oral pressure probe 30, described hereinabove with reference to FIGS. 1A-B and 5A-B, in accordance with an application of the present invention. In this configuration, oral pressure probe 30 comprises a flow-through pressure probe 82. FIG. 7A is a view of the side of flow-through pressure probe 82 facing away from the subject's face, and FIG. 7B is a view of the side of flow-through pressure probe 82 facing toward the subject's face. The techniques described herein with reference to the other figures may also be implemented using oral pressure probes other than flow-through pressure probe 82.

Flow-through pressure probe 82 comprises a baffle 83, which is shaped so as to define a concave chamber 84 open on one side 86 for positioning in front of mouth 54 of subject 52. Concave chamber 84 is shaped so to define one or more openings 88 that pass entirely through a wall 90 of concave chamber 84 to the other side 92 of concave chamber 84. The one or more openings 88 provide a low level of resistance to airflow, thereby allowing subject to breathe comfortably while wearing flow-through pressure probe 82, such as during sleep. Wall 90 may be shaped so as to define, or may comprise, a mesh that defines the one or more openings 88.

Oral-pressure tube 32 is in fluid communication with side 86 of concave chamber 84, such that a portion of the airflow from mouth 54 passes into oral-pressure tube 32. For applications in which oral pressure sensor 23 comprises a differential pressure sensor, oral pressure sensor 23 may be open to the environment via oral-pressure tube 32 and the one or more openings 88. The oral differential is obtained by generating a pressure drop across the one or more openings 88 a mesh, as is known in pneumotachography, which is conventionally used, for example, in obstructive apnea and hypopnea detection.

For some applications, concave chamber 84 is shaped so to define at least 5, no more than 128, and/or between 5 and 128 openings 88 that pass entirely through wall 90 of concave chamber 84 to the other side 92 of concave chamber 84.

For some applications, openings 88 have:
an average cross-sectional area of at least 0.5 mm2, no more than 20 mm2, and/or between 0.5 and 20 mm2,
an aggregate cross-sectional area of at least 50 mm2, no more than 70 mm2, and/or between 50 and 70 mm2, and/or
an average length of at least 1 mm2, no more than 3.5 mm2, and/or between 1 and 3.5 mm2.

For some applications, side 86 of baffle 83 has a surface area, including openings 88, of at least 800 mm2, no more than 1200 mm2, and/or between 800 and 1200 mm2. Alternatively or additionally, for some applications, the aggregate cross-sectional area of openings 88 is at least 50%, no more than 70%, and/or between 50% and 70% of the surface area of side 86 of baffle 83, including openings 88.

For example, flow-through pressure probe 82 may comprise silicone, another soft material, or a harder material.

Figure 10:
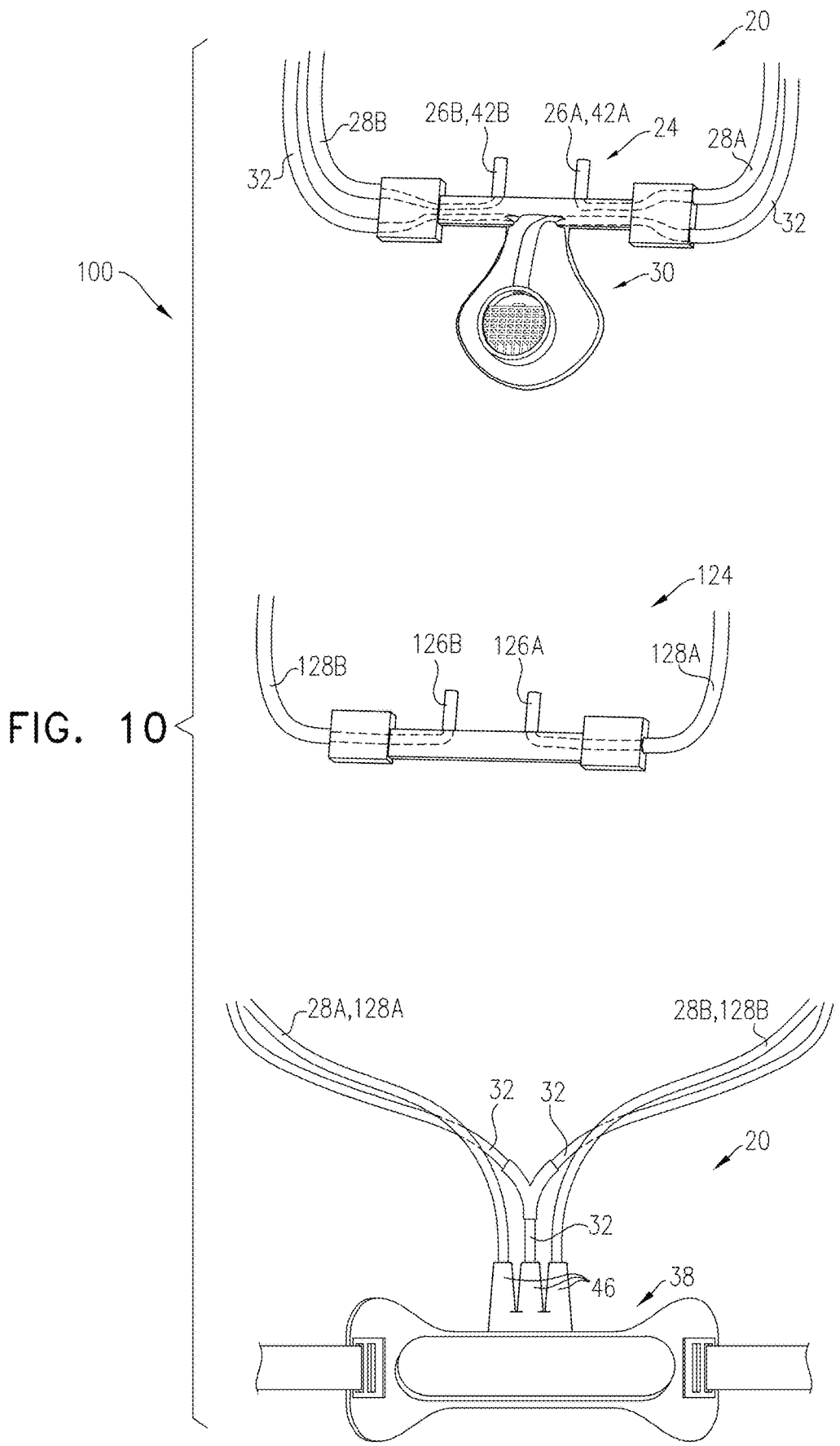
FIG. 10 is a schematic illustration of a nasal-cycle measurement kit, in accordance with an application of the present invention.

Reference is now made to FIG. 10, which is a schematic illustration of a nasal-cycle measurement kit 100, in accordance with an application of the present invention. Kit 100 comprises nostril-oral probe assembly 24, described hereinabove with reference to FIGS. 1A-B, 2, and 5A-B. Optionally, kit 100 further comprises at least a portion of the other elements of nasal-cycle measurement device 20, described hereinabove with reference to FIGS. 1A-6.

Kit 100 further comprises a nostril probe assembly 124, which comprises
a left-nostril pressure probe 126A, which is configured to be inserted into the left nostril, and comprises a left-nostril-pressure tube 128A that is configured to transmit a left-nostril pressure wave from the left nostril to left-nostril pressure sensor 22A; and
a right-nostril pressure probe 126B, which is configured to be inserted into the right nostril, and comprises a right-nostril-pressure tube 128B that is configured to transmit a right-nostril pressure wave from the right nostril to right-nostril pressure sensor 22B.

However, nostril probe assembly 124, unlike nostril-oral probe assembly 24, is not configured to measure airway flow in the mouth, and thus does not comprise an oral pressure probe (and typically does not comprise an oral-pressure tube). As a result, nostril probe assembly 124 may be somewhat more comfortable to wear and provide better access to the mouth for eating and drinking, than nostril-oral probe assembly 24. Moreover, people do not stop breathing during the day, so weight of the laterality index based oral airflow is not necessary.

Nostril probe assembly 124 may implement any of the other features of nostril-oral probe assembly 24, mutatis mutandis.

Typically, before use of nostril probe assembly 124, left-nostril-pressure tube 128A and right-nostril-pressure tube 128*b* are coupled in fluid communication with two of the three pneumatic connectors 46 of housing 38 of nasal-cycle measurement device 20. If left-nostril-pressure tube 28A, right-nostril-pressure tube 28B, and oral-pressure tube 32 of nostril-oral probe assembly 24 were previously coupled to the three pneumatic connectors 46 of housing, these tubes are removed before coupling the tubes of nostril probe assembly 124 to two of the three pneumatic connectors 46.

During a typical 24-hour measurement session, nostril probe assembly 124 is coupled to housing 38 as described above during periods in which the subject is awake, and nostril-oral probe assembly 24 is coupled to housing 38 as described above during periods in which the subject is sleeping, such as at night (or about to go to sleep, such as at night).

The one or more of processors 14 and/or 66 are configured to:
- utilize measurements from all three of left-nostril, right-nostril, and oral pressure sensors 22A, 22B, and 23 when nostril-oral probe assembly 24 is connected to pneumatic connectors 46 (via left-nostril-pressure tube 28A, right-nostril-pressure tube 28B, and oral-pressure tube 32), and
- utilize measurements from left-nostril and right-nostril pressure sensors 122A and 122B when nostril probe assembly 124 is connected to two of pneumatic connectors 46 (via left-nostril-pressure tube 128A and right-nostril-pressure tube 128B).

For example, processor 36 and/or 66 may be configured to receive an instruction, such as from an external software application, indicating which probe assembly is connected. Alternatively or additionally, processor 36 and/or 66 may be configured to receive an input, such as from a user control button or switch, indicating which probe assembly is connected. Further alternatively or additionally, processor 36 and/or 66 may be configured to automatically detect which probe assembly is connected by periodically or constantly sensing whether oral pressure sensor 23 is connected to one of pneumatic connectors 46, by sensing whether a signal is detectable or by sensing that oral-pressure tube 32 is connected to one of pneumatic connectors 46.

Typically, the one or more of processors 14 and/or 36 are configured:
- when nostril-oral probe assembly 24 is connected to pneumatic connectors 46, to calculate the series of orally-weighted laterality-indices, described hereinabove with reference to FIGS. 1A-B and 2, based on the left-nostril, the right-nostril, and the oral airflows, and
- when nostril-oral probe assembly 124 is connected to two of pneumatic connectors 46, to calculate a series of laterality-indices that are not orally-weighted, based on the left-nostril and the right-nostril airflows.

Reference is again made to FIGS. 1A-5B. For some applications, the one or more of processors 14 and/or 36 are configured to perform calibration for the individual user of nasal-cycle measurement system 10 before performing the measurement and calculations described herein. As described above, the pressure probes measure respective pressures, which are converted to respective airflows. The calibration finds pressure-to-flow correspondences. For left- and right-nostril pressure probes 26A and 26B, this conversion depends on the diameter of the nostril in which the probe is placed, and, moreover, is susceptible to intra-nostril deformities that are not visible from outside the nostrils.

Reference is now made to FIGS. 11A and 11B, which are schematic illustrations of a calibration wand 200 for performing the calibration described immediately above, in accordance with an application of the present invention. Calibration wand 200 typically utilizes known pneumotachography principles (e.g., see Pols W, Pneumotachography. Acta Anaesthesiologica Scandinavica 6, 171-179 (1962)), albeit implemented in a new way. Calibration wand 200 comprises a tube 210 (e.g., having an 8 mm internal diameter). Calibration wand 200 is shaped so as to define a tip 212 that conforms to the outer nostril so as to form an air-tight seal with the outer nostril, without being inserted into the nostril. To this end, tip 212 is shaped as a partial ellipsoid, such as a partial sphere, as shown. A distal end 218 of tube 210 is open through a distal portion of tip 212, typically centered on the tip.

During calibration, calibration wand 200 is connected to one of pneumatic connectors 46 of housing 38 instead of left-nostril, right-nostril, and oral pressure probes 26A, 26B, and 30. Calibration wand 200 may be connected to the one of pneumatic connectors 46 either directly or via two tubes similar to left-nostril-pressure and right-nostril-pressure tubes 28A and 28B. At the point at which the pneumatic connector or tubes connects to openings 216 of calibration wand 200, the wand has an internal mesh 214.

Because calibration wand 200 has a known internal diameter, the pressure measurements it generates are transformed to flow, such as based on a look-up table. Because tip 212 of calibration wand 200 make an air-tight seal with the nostrils, the pressure measurement reflect actual flow rates that are used to calibrate the somewhat leaky flow measured using left-nostril and right-nostril pressure probes 26A and 26B, as described below.

The user is instructed (such as by the application and/or a healthcare worker) to sit comfortably and calmly, hold tip 212 of calibration wand 200 against left nostril 50A without inserting the tip into the nostril, and breath with his or her mouth shut for a period of time, e.g., one minute. Next, the user shifts the wand to his or her right nostril, and again breathes with his or her mouth shut for a period of time, e.g., one minute. Finally, the user puts the wand in his or her mouth, pinches his or her nose shut, and breathes for a period of time, e.g., one minute.

After this process, the user disconnects calibration wand 200 from the one of pneumatic connectors 46 and instead connects nostril-oral probe assembly 24 to pneumatic connectors 46, and inserts left-nostril and right-nostril pressure probes 26A and 26B into the left and right nostrils. The user again breathes calmly for a period of time, e.g., one minute, with his or her mouth shut. This enables calibration of both nasal pressure sensors 22A and 22B, by matching the flow values with the probe to those with calibration wand 200. Finally, the user again pinches his or her nose shut, now with nostril-oral probe assembly 24 connected to pneumatic connectors 46, and again breathes calmly for a period of time, e.g., one minute. This allows for the oral calibration. Thus, a several-minute process allows user calibration, allowing results to be reported in milliliters per second (ml/s) of flow, rather than in arbitrary pressure units.

Optionally, the one or more of processors 14 and/or 36 are configured to check that the patient does not change nostril favoring during calibration.

The techniques described herein as being performed by the one or more of processors 14, processor 36, and/or processor 66 may be implement in implemented in hardware and/or software. Software may optionally be stored in a computer-readable storage medium, which may be a tangible device that can retain and store instructions for use by an instruction execution device. The computer readable storage medium may be, for example, but is not limited to, an electronic storage device, a magnetic storage device, an optical storage device, an electromagnetic storage device, a semiconductor storage device, or any suitable combination of the foregoing. A non-exhaustive list of more specific examples of the computer readable storage medium includes the following: a portable computer diskette, a hard disk, a random access memory (RAM), a read-only memory (ROM), an erasable programmable read-only memory (EPROM or Flash memory), a static random access memory (SRAM), a portable compact disc read-only memory (CD-ROM), a digital versatile disk (DVD), a memory stick, a floppy disk, a mechanically encoded device such as punch-cards or raised structures in a groove having instructions recorded thereon, and any suitable combination of the foregoing. A computer readable storage medium, as used herein, is not to be construed as being transitory signals per se, such as radio waves or other freely propagating electromagnetic waves, electromagnetic waves propagating through a waveguide or other transmission media (e.g., light pulses passing through a fiber-optic cable), or electrical signals transmitted through a wire.

Computer readable program instructions described herein can be downloaded to respective computing/processing devices from a computer readable storage medium or to an external computer or external storage device via a network, for example, the Internet, a local area network, a wide area network and/or a wireless network. The network may comprise copper transmission cables, optical transmission fibers, wireless transmission, routers, firewalls, switches, gateway computers and/or edge servers. A network adapter card or network interface in each computing/processing device receives computer readable program instructions from the network and forwards the computer readable program instructions for storage in a computer readable storage medium within the respective computing/processing device.

Computer readable program instructions for carrying out operations of the present invention may be assembler instructions, instruction-set-architecture (ISA) instructions, machine instructions, machine dependent instructions, microcode, firmware instructions, state-setting data, or either source code or object code written in any combination of one or more programming languages, including an object oriented programming language such as SMALLTALK, C++ or the like, and conventional procedural programming languages, such as the "C" programming language or similar programming languages. The computer readable program instructions may execute entirely in the one or more of processors 14, entirely in processor 36, entirely in processor 66, or partially in two or more of these processors, and/or another remote computer, or entirely on the remote computer or server. In the latter scenario, the remote computer may be connected to the one or more of processors 14, 36, and/or 66 through any type of network, including a local area network (LAN) or a wide area network (WAN), or the connection may be made to an external computer (for example, through the Internet using an Internet Service Provider).

Certain aspects of the present invention may be implemented by computer readable program instructions. These computer readable program instructions may be provided to a processor of a general-purpose computer, special purpose computer, or other programmable data processing apparatus to produce a machine, such that the instructions, which execute via the processor of the computer or other programmable data processing apparatus, create means for implementing the functions/acts specified in the flowchart and/or block diagram block or blocks. These computer readable program instructions may also be stored in a computer readable storage medium that can direct a computer, a programmable data processing apparatus, and/or other devices to function in a particular manner, such that the computer readable storage medium having instructions stored therein comprises an article of manufacture including instructions which implement aspects of the function/act described herein.

The computer readable program instructions may also be loaded onto a computer, other programmable data processing apparatus, or other device to cause a series of operational steps to be performed on the computer, other programmable apparatus or other device to produce a computer implemented process, such that the instructions which execute on the computer, other programmable apparatus, or other device implement the functions/acts described herein.

In some applications, the device may function as a "nasal Holter monitor," and the techniques described herein may be used for performing upper airway diagnosis, alternatively or additionally to the other uses described hereinabove. For example, the device can determine whether left or right nostril tend to congest over the recording period.

In case of conflict between definitions provided herein and those provided in the above-mentioned article by Kahana-Zweig R et al., the definitions provided herein will prevail.

It will be appreciated by persons skilled in the art that the present invention is not limited to what has been particularly shown and described hereinabove. Rather, the scope of the present invention includes both combinations and subcombinations of the various features described hereinabove, as well as variations and modifications thereof that are not in the prior art, which would occur to persons skilled in the art upon reading the foregoing description.

The invention claimed is:

1. Apparatus comprising:
   a left-nostril pressure sensor, a right-nostril pressure sensor, and an oral pressure sensor;
   a nostril-oral probe, which comprises:
      a left-nostril pressure probe, which is configured to be inserted into a left nostril of a subject, and comprises a left-nostril-pressure tube that is configured to transmit a left-nostril pressure wave from the left nostril to the left-nostril pressure sensor;
      a right-nostril pressure probe, which is configured to be inserted into a right nostril of the subject, and comprises a right-nostril-pressure tube that is configured to transmit a right-nostril pressure wave from the right nostril to the right-nostril pressure sensor; and
      an oral pressure probe, which is configured to be positioned in air communication with a mouth of the subject, and comprises an oral-pressure tube that is configured to transmit an oral pressure wave from the mouth to the oral pressure sensor;
   a memory, which is configured to store left-nostril, right-nostril, and oral pressures sensed by the left-nostril pressure sensor, the right-nostril pressure sensor, and the oral pressure sensor, respectively, over a total period having a duration of at least 12 hours; and
   one or more processors, which are configured:
      to convert the left-nostril, the right-nostril, and the oral pressures stored in the memory to left-nostril, right-nostril, and oral pressure airflows, respectively, and to calculate, based on the left-nostril, the right-nostril, and the oral airflows, a series of orally-weighted laterality-indices over a respective series of sub-periods of the total period,
wherein each of the orally-weighted laterality-indices of each of the sub-periods is indicative of a laterality index over the sub-period weighted by a normalized oral airflow over the sub-period, such that the greater the normalized oral airflow, the smaller the orally-weighted laterality-index, and
wherein each of the orally-weighted laterality-indices of each of the sub-periods reflects relative airflow through the left and the right nostrils over the sub-period.

2. The apparatus according to claim 1, wherein the one or more processors are configured to calculate an overall orally-weighted laterality index equal to an average of the orally-weighted laterality-indices during the total period.

3. The apparatus according to claim 2, further comprising a wireless transmitter, which is configured to transmit a wireless signal indicative of the overall orally-weighted laterality index.

4. The apparatus according to claim 1, wherein the one or more processors are configured to calculate an overall orally-weighted laterality index equal to an average of respective absolute values of the orally-weighted laterality-indices during the total period.

5. The apparatus according to claim 1, wherein each of the sub-periods has a duration of between 30 and 180 seconds.

6. The apparatus according to claim 1, wherein the duration of the total period is at least 24 hours.

7. The apparatus according to claim 1, wherein the oral pressure probe is configured to be positioned outside the mouth in the air communication with the mouth.

8. The apparatus according to claim 1,
further comprising a posture sensor that is configured to separately sense body posture and head posture,
wherein the one or more processors are configured to calculate each of the orally-weighted laterality-indices of each of the sub-periods partially in response to the sensed body posture and the sensed head posture such that each of the sub-periods is associated with a given combination of the sensed body posture and head posture.

9. The apparatus according to claim 1, wherein the one or more processors are configured to calculate each of the laterality indices of each of the sub-periods by dividing (a) a difference between the left-nostril airflow and the right-nostril airflow over the sub-period by (b) a sum of the left-nostril airflow and the right-nostril airflow over the sub-period.

10. The apparatus according to claim 1, wherein the one or more processors are configured to weight each of the orally-weighted laterality-indices of each of the sub-periods by multiplying (a) the laterality index by (b) (i) a difference between 1 and an absolute value of the normalized oral airflow, over the sub-period (ii) raised to a power less than 1.

11. The apparatus according to claim 10, wherein the power is no more than 0.5.

12. The apparatus according to claim 11, wherein the power equals 0.25.

13. The apparatus according to claim 1, further comprising:
a housing, configured to be coupled to skin of a nape of a subject; and
exactly one position sensor, which is configured to sense a position of the position sensor with at least three degrees of freedom and provide at least three position-sensor outputs, and which is disposed within the housing,
wherein the one or more processors are configured to:
ascertain, using the position-sensor outputs when the housing is coupled to the skin of the nape, body posture of the subject and, separately, head posture of the subject, and
generate one or more posture outputs indicative of the body posture and the head posture.

14. The apparatus according to claim 1, further comprising:
a housing, configured to be coupled to skin of a nape of a subject; and
at least one position sensor, which is configured to sense a position of the position sensor and provide position-sensor outputs, and is disposed within the housing,
wherein the one or more processors are configured to:
ascertain, using the position-sensor outputs when the housing is coupled to the skin of the nape, body posture of the subject and, separately, head posture of the subject,
based on the body posture and the head posture, select a combined posture of the subject from a plurality of predetermined possible combined postures that reflect both the body posture and the head posture, wherein the one or more processors are configured such that the plurality of predetermined possible combined postures includes: upright, lying with a face facing left, and lying with the face facing right, and
generate a posture output indicative of the combined posture of the subject.

15. A method comprising:
inserting a left-nostril pressure probe of a nostril-oral probe into a left nostril of a subject, such that a left-nostril-pressure tube transmits a left-nostril pressure wave from the left nostril to a left-nostril pressure sensor;
inserting a right-nostril pressure probe of the nostril-oral probe into a right nostril of the subject, such that a right-nostril-pressure tube transmits a right-nostril pressure wave from the right nostril to a right-nostril pressure sensor;
positioning an oral pressure probe of the nostril-oral probe in air communication with a mouth of the subject, such that an oral-pressure tube transmits an oral pressure wave from the mouth to an oral pressure sensor; and
activating one or more processors:
to store, in a memory, left-nostril, right-nostril, and oral pressures sensed by the left-nostril pressure sensor, the right-nostril pressure sensor, and the oral pressure sensor, respectively, over a total period having a duration of at least 12 hours,
to convert the left-nostril, the right-nostril, and the oral pressures stored in the memory to left-nostril, right-nostril, and oral pressure airflows, respectively, and
to calculate, based on the left-nostril, the right-nostril, and the oral airflows, a series of orally-weighted laterality-indices over a respective series of sub-periods of the total period,
wherein each of the orally-weighted laterality-indices of each of the sub-periods is indicative of a laterality index over the sub-period weighted by a normalized oral airflow over the sub-period, such that the greater the normalized oral airflow, the smaller the orally-weighted laterality-index, and wherein each of the orally-weighted laterality-indices of each of the sub-periods reflects relative airflow through the left and the right nostrils over the sub-period.

16. The method according to claim 15, wherein activating the one or more processors comprises activating the one or more processors to calculate an overall orally-weighted laterality index equal to an average of the orally-weighted laterality-indices during the total period.

17. The method according to claim 15, wherein activating the one or more processors comprises activating the one or more processors to calculate an overall orally-weighted laterality index equal to an average of respective absolute values of the orally-weighted laterality-indices during the total period.

18. The method according to claim 15, wherein positioning the oral pressure probe in the air communication with the mouth comprises positioning the oral pressure probe outside the mouth in the air communication with the mouth.

19. The method according to claim 15, wherein activating the one or more processors comprises activating the one or more processors to:
separately sense body posture and head posture, using a posture sensor, and calculate each of the orally-weighted laterality-indices of each of the sub-periods partially in response to the sensed body posture and the sensed head posture such that each of the sub-periods is associated with a given combination of the sensed body posture and head posture.

20. The method according to claim 15, wherein activating the one or more processors comprises activating the one or more processors to calculate each of the laterality indices of each of the sub-periods by dividing (a) a difference between the left-nostril airflow and the right-nostril airflow over the sub-period by (b) a sum of the left-nostril airflow and the right-nostril airflow over the sub-period.

21. The method according to claim 15, wherein activating the one or more processors comprises activating the one or more processors to weight each of the orally-weighted laterality-indices of each of the sub-periods by multiplying (a) the laterality index by (b) (i) a difference between 1 and an absolute value of the normalized oral airflow over the sub-period (ii) raised to a power less than 1.

22. The method according to claim 15,
wherein the method further comprises coupling a housing to skin of a nape of a subject such that at least one position sensor within the housing is positioned over one or more of a first cervical vertebra (C1), a second cervical vertebra (C2), a third cervical vertebra (C3), and a fourth cervical vertebra (C4) of the subject, without being positioned over any vertebrae below the C4 vertebra, wherein the at least one position sensor is configured to sense a position of the position sensor and provide position-sensor outputs, and
wherein activating the one or more processors comprises activating the one or more processors to (a) ascertain, using the position-sensor outputs when the housing is coupled to the skin of the nape, body posture of the subject and, separately, head posture of the subject, and (b) generate one or more posture outputs indicative of the body posture and the head posture.

\* \* \* \* \*